(12) United States Patent
Waydo

(10) Patent No.: US 10,201,286 B2
(45) Date of Patent: Feb. 12, 2019

(54) FREQUENCY DOMAIN PROJECTION ALGORITHM

(71) Applicant: Apple Inc., Cupertino, CA (US)

(72) Inventor: Stephen J. Waydo, Campbell, CA (US)

(73) Assignee: Apple Inc., Cupertino, CA (US)

(*) Notice: Subject to any disclaimer, the term of this patent is extended or adjusted under 35 U.S.C. 154(b) by 837 days.

(21) Appl. No.: 14/466,914

(22) Filed: Aug. 22, 2014

(65) Prior Publication Data

US 2016/0051157 A1 Feb. 25, 2016

(51) Int. Cl.
*A61B 5/00* (2006.01)
*A61B 5/024* (2006.01)
*A61B 5/11* (2006.01)

(52) U.S. Cl.
CPC ............ *A61B 5/02416* (2013.01); *A61B 5/11* (2013.01); *A61B 5/721* (2013.01); *A61B 5/7221* (2013.01); *A61B 5/7246* (2013.01)

(58) Field of Classification Search
CPC ...................................................... A61B 5/02
See application file for complete search history.

(56) References Cited

U.S. PATENT DOCUMENTS

| 5,483,261 A | 1/1996 | Yasutake |
| 5,488,204 A | 1/1996 | Mead et al. |
| 5,825,352 A | 10/1998 | Bisset et al. |
| 5,835,079 A | 11/1998 | Shieh |
| 5,880,411 A | 3/1999 | Gillespie et al. |
| 6,188,391 B1 | 2/2001 | Seely et al. |
| 6,310,610 B1 | 10/2001 | Beaton et al. |
| 6,323,846 B1 | 11/2001 | Westerman et al. |
| 6,690,387 B2 | 2/2004 | Zimmerman et al. |
| 7,015,894 B2 | 3/2006 | Morohoshi |
| 7,184,064 B2 | 2/2007 | Zimmerman et al. |
| 7,663,607 B2 | 2/2010 | Hotelling et al. |
| 8,479,122 B2 | 7/2013 | Hotelling et al. |
| 2003/0225337 A1* | 12/2003 | Scharf ................ A61B 5/14551 600/508 |

(Continued)

FOREIGN PATENT DOCUMENTS

| JP | 2000-163031 A | 6/2000 |
| JP | 2002-342033 A | 11/2002 |

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

(Continued)

*Primary Examiner* — Serkan Akar
(74) *Attorney, Agent, or Firm* — Morrison & Foerster LLP

(57) ABSTRACT

An algorithm for determining heart rate by removing motion artifacts from a PPG signal in the frequency domain utilizes a principal component analysis. Some examples of the present disclosure process PPG signals in combination with accelerometer signals to remove unwanted artifacts in the frequency domain. For example, principal components of the accelerometer signal can be generated and combined with the PPG signal to filter out acceleration contributions represented in the PPG signal to reveal heart rate peaks. Additionally, in some examples, templates may be stored for correlation with candidate heart rate peaks to select those peaks with the highest correlations with the stored templates.

17 Claims, 12 Drawing Sheets

(56) References Cited

U.S. PATENT DOCUMENTS

| | | | |
|---|---|---|---|
| 2005/0113703 A1* | 5/2005 | Farringdon | A61B 5/0428 600/509 |
| 2006/0197753 A1 | 9/2006 | Hotelling | |
| 2007/0208265 A1* | 9/2007 | Couderc | A61B 5/7253 600/512 |
| 2011/0066042 A1* | 3/2011 | Pandia | A61B 5/029 600/484 |
| 2012/0065524 A1* | 3/2012 | Morren | A61B 5/1102 600/484 |
| 2014/0275854 A1* | 9/2014 | Venkatraman | A61B 5/721 600/301 |

OTHER PUBLICATIONS

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

\* cited by examiner

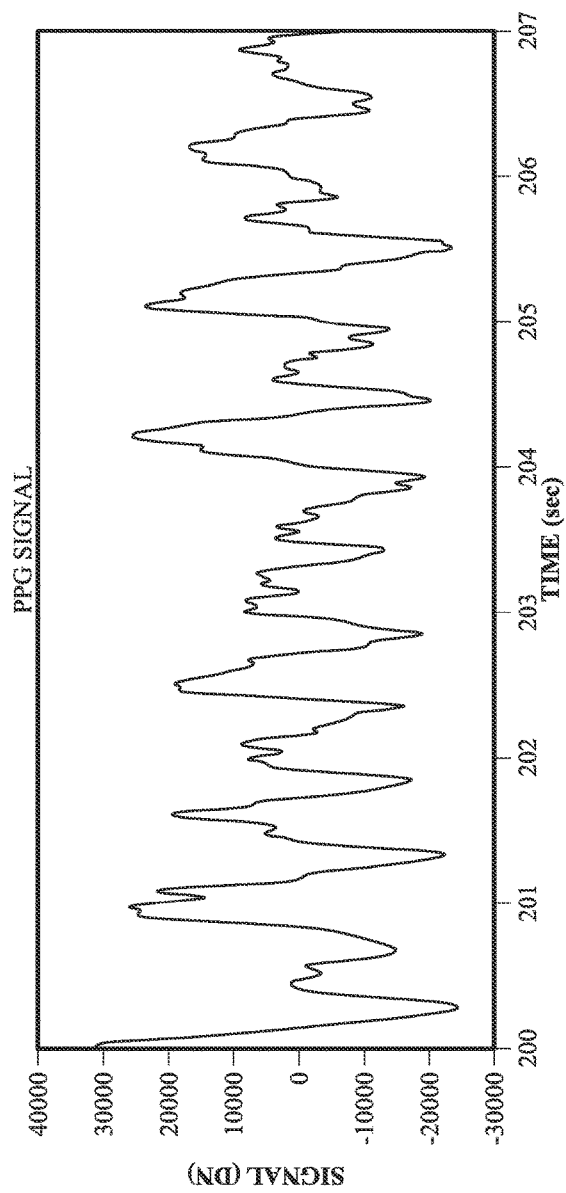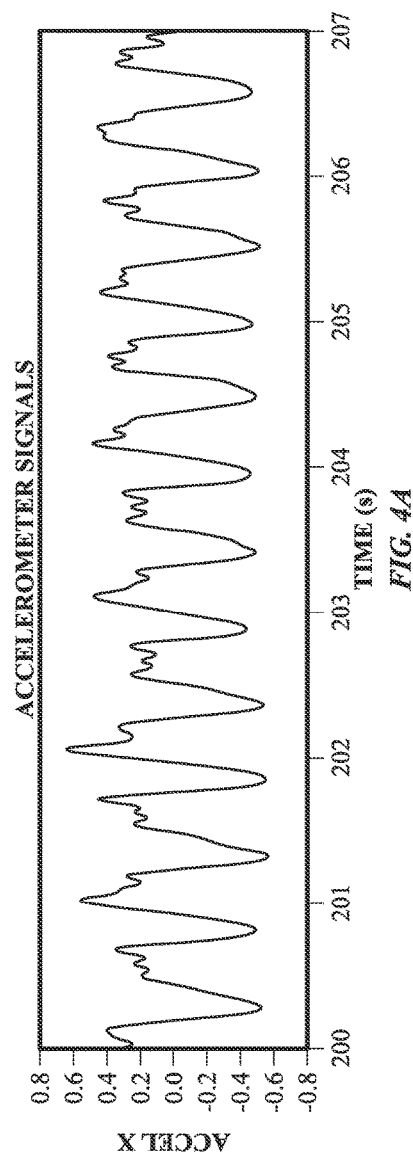
FIG. 3
FIG. 4A

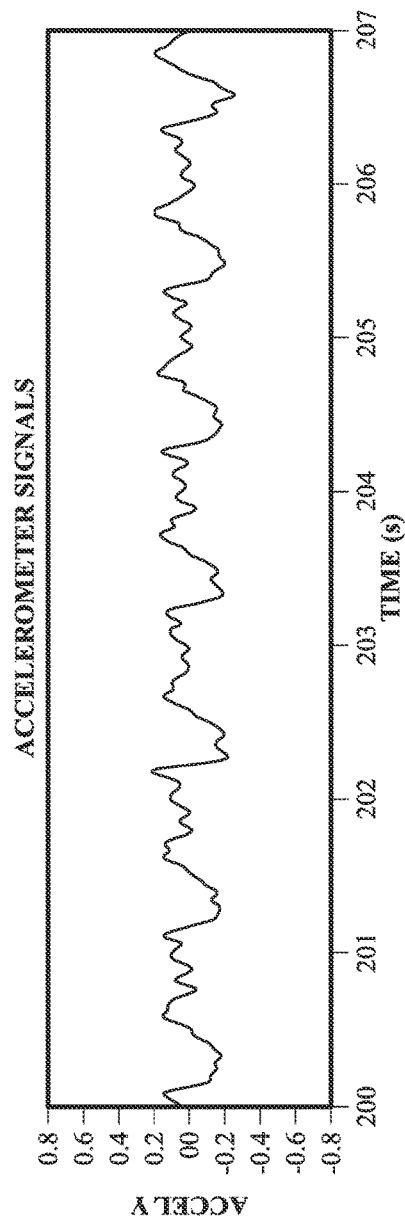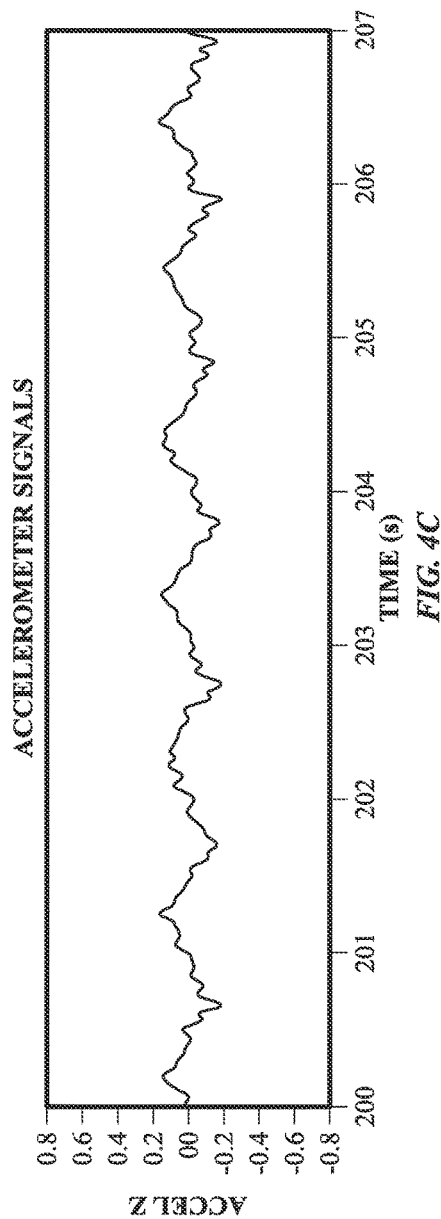
FIG. 4B
FIG. 4C

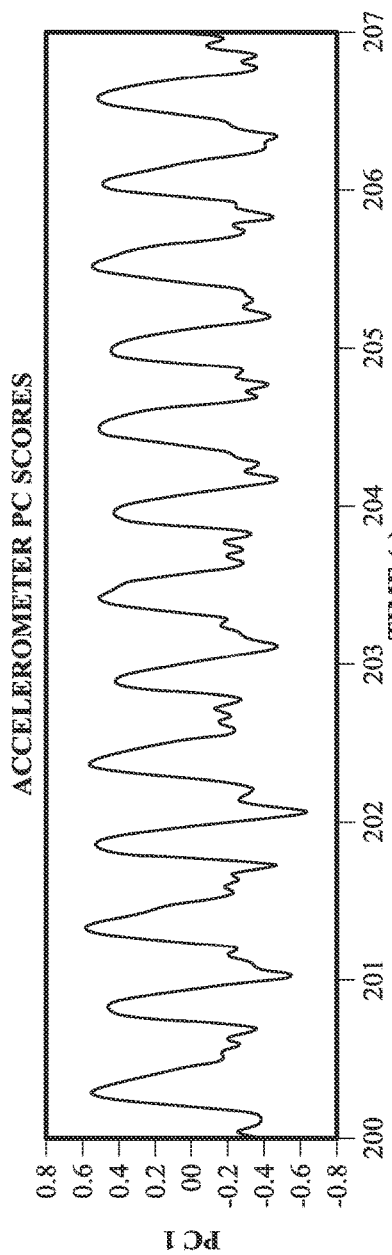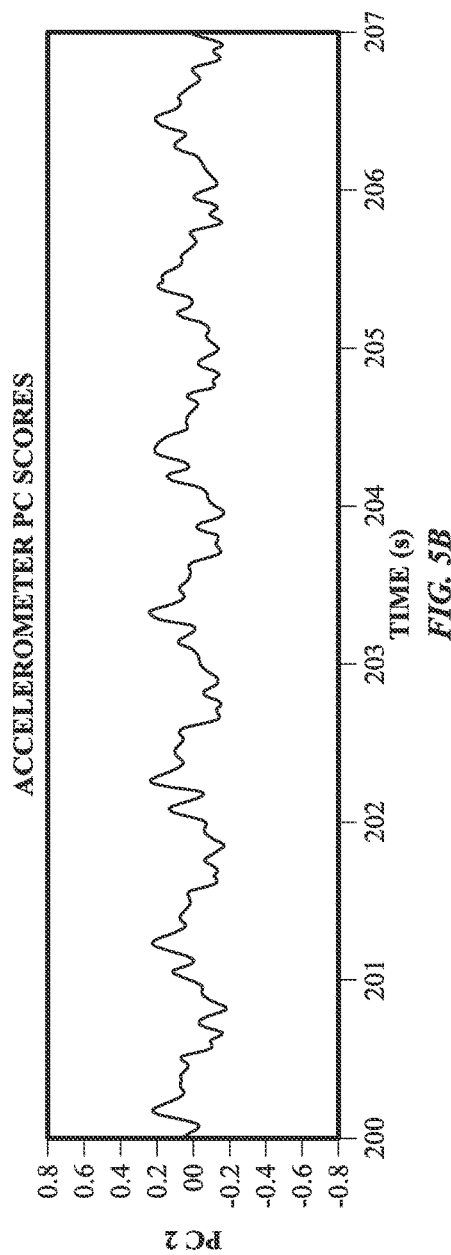
FIG. 5A
FIG. 5B

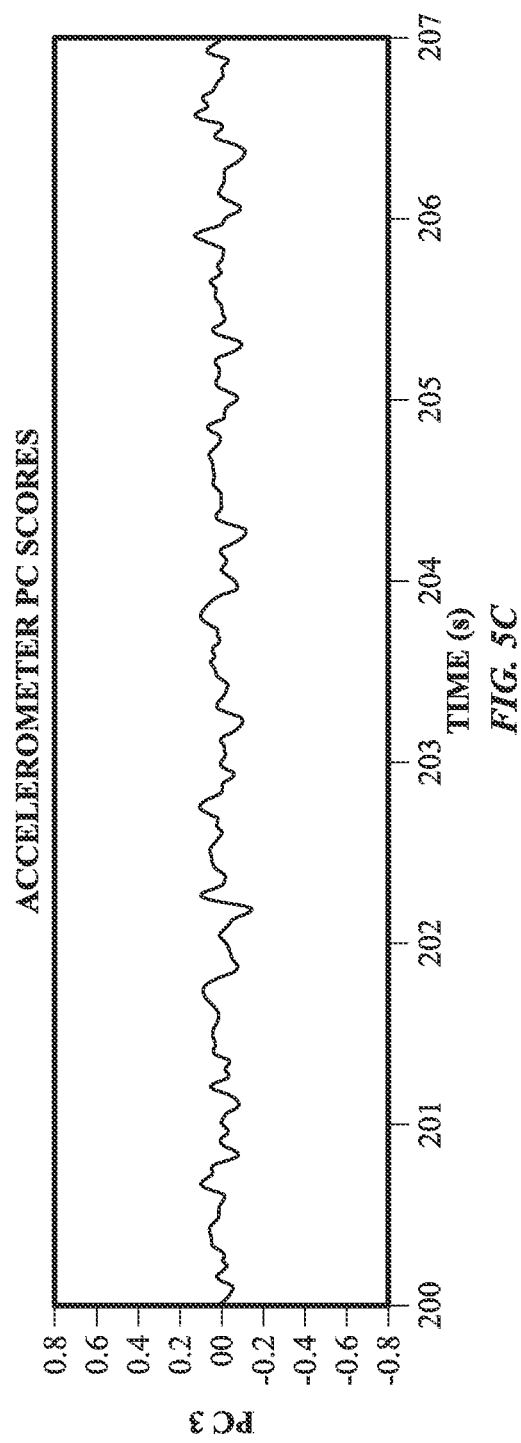

100,201,286 B2

FREQUENCY DOMAIN PROJECTION ALGORITHM

FIELD OF THE DISCLOSURE

This relates generally to processing of a photoplethysmogram (PPG) signal and, more specifically, to using frequency domain projection (FDP) to determine heart rate.

BACKGROUND OF THE DISCLOSURE

A photoplethysmogram (PPG) signal can be obtained from a pulse oximeter, which employs a light emitter and a light sensor to measure the perfusion of blood to the skin of a user. The PPG signal can be compromised by noise due to motion (e.g., acceleration) artifacts. That is, movement of the body of a user can cause the skin and vasculature to expand and contract, introducing acceleration artifacts into the PPG signal. As a result, motion artifacts can make it difficult to effectively determine a user's heart rate.

BRIEF SUMMARY OF THE DISCLOSURE

This relates to removing motion artifacts from the PPG signal using frequency domain projection (FDP) to determine heart rate. The PPG signals, sometimes referred to as raw PPG signals, may be considered as having heart rate (HR) components and motion (acceleration) artifact components. Some examples of the present disclosure utilize an accelerometer to provide accelerometer signals to measure movements of the user and signal processing of the raw PPG signals in combination with the accelerometer signals to remove unwanted motion artifacts in the frequency domain. For example, one may transform the time domain raw PPG signals and the time domain accelerometer signals into the frequency domain (FD) to produce FD raw PPG signals and FD accelerometer signals. The FD raw PPG signals have a HR component and a motion (acceleration) artifact component. After transformation into the FD, the motion (acceleration) artifact components may be projected out of the FD raw PPG signals to remove or minimize these motion artifact components. Projecting out the FD motion artifact components may be achieved by individually scaling peaks of the FD accelerometer signals from different acceleration axes and performing a process, such as least square fitting of the scaled FD acceleration signals, to subtract out or minimize the FD motion artifact components from the FD raw PPG signals. In other examples FD principal components of the FD accelerometer signals can be generated to assist in separating out discrete frequency modes from the FD acceleration signals. The FD principal components may then be used to project out the FD motion artifact components from the FD raw PPG signals. The resulting FD projected PPG signals may show much enhanced HR peaks which can be readily differentiated from residual acceleration artifact components and noise. Additionally, in some examples, pre-stored templates can be correlated with the projected PPG signals to determine a predicted heart rate. In yet other examples, tracking of the determined HR and associated confidence level may be used to dynamically adjust a sampling window to improve accuracy of measurements or minimize latency.

BRIEF DESCRIPTION OF THE DRAWINGS

FIG. 3 illustrates an exemplary time domain representations of raw PPG signals according to examples of the disclosure.

FIGS. 4A-4C illustrate exemplary time domain representations of acceleration signals along the x, y and z axes according to examples of the disclosure.

FIGS. 5A-5C illustrate exemplary time domain acceleration scores along the principal component axes PC1-PC3 corresponding to the acceleration signals of FIGS. 4A-4C, respectively.

DETAILED DESCRIPTION OF THE DISCLOSURE

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

A photoplethysmogram (PPG) signal can be obtained from a pulse oximeter, which employs a light emitter and a light sensor to measure the perfusion of blood to the skin of a user. However, the signal can be compromised by noise due to motion artifacts especially artifacts caused by acceleration. That is, movement of the body of a user can cause the skin and vasculature to expand and contract, introducing noise into the signal. To address the presence of motion artifacts, some examples of the present disclosure utilize an accelerometer to measure acceleration (movements) of the user and signal processing of the raw PPG signal in combination with the accelerometer signal to remove unwanted artifacts in the frequency domain. In some examples, a principal component analysis may be performed on the x, y, z acceleration signals to obtain principal components of the accelerometer signals (e.g., PC1, PC2). The raw PPG signals and the principal components can be transformed into the frequency domain, and these FD principal components can be combined with the FD raw PPG signal to filter out acceleration contributions present in the FD raw PPG signal to obtain FD projected PPG signals free of the motion artifacts. Additionally, in template matching examples, pre-stored templates can be correlated with the FD projected PPG signals to determine heart rate having the highest correlation with the stored templates. In other examples, a sampling window may be dynamically adjusted based on the determined HR and its associated confidence level either with or without template matching.

Figure 1:
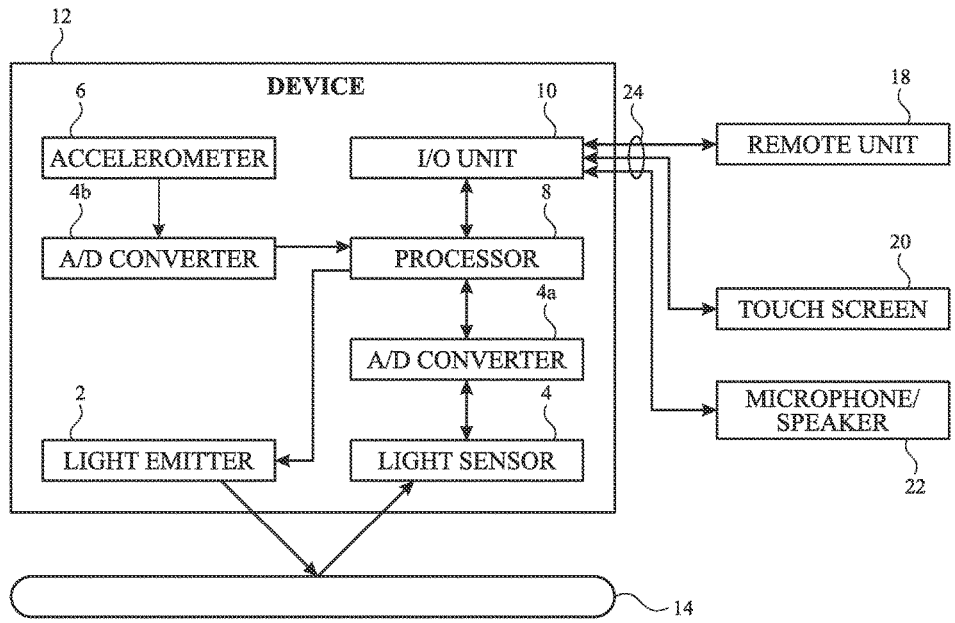
FIG. 1 shows an overall block diagram of the frequency domain projection analysis employed to determine heart rate used in various examples of the disclosure.

FIG. 1 illustrates an exemplary block diagram of a system for determining heart rate using FDP according to examples of the disclosure. As illustrated in FIG. 1, the block diagram can include a light emitter 2, light sensor 4, analog-to-digital (A/D) converters 4a and 4b, accelerometer 6, processor 8 and input/output (I/O) unit 10. These components can be incorporated within a physical device 12 that can be worn or held by a user so as to secure the device to a user's skin (a limb, for example) or otherwise attached to an article of clothing worn by the user, with the light emitter 2 and light sensor 4 positioned proximate to a user's skin. Alternately, the device 12 can be entirely or partially incorporated within a smartphone or other portable device such that a user can hold the smartphone in a manner to cause the below described light beam to be reflected from the user's skin back into a light sensor positioned within the smartphone itself. A portion of the light from light emitter 2 can be absorbed by the skin, vasculature, and/or blood, among other possibilities, and a portion can be reflected back to a light sensor 4 co-located with the light emitter. The signals from the sensor 4 can include heart rate signals due to the blood pulse wave.

Although illustrated in FIG. 1 as having only a single light emitter 2 and light sensor 4, in other examples multiple channels can be used in the system. The multiple channels can be created by increasing the number of emitter/sensor pairs, where each emitter/sensor pair can create a new channel, for example. In other examples, multiple channels can be created using different light paths from one emitter to multiple sensors (e.g., one emitter and five sensors can produce five light paths). In yet other examples, multiple channels can be created using different light paths from multiple emitters to multiple sensors (e.g., two emitters and two sensors can produce four light paths including two paths from a first emitter to each of the two sensors and two paths from a second emitter to each of the two sensors). The one or more light emitters can produce light in ranges corresponding to infrared (IR), green, amber, blue and/or red light, among other possibilities. In some examples, a light emitter can be a light emitting diode (LED) and a light sensor can be a photodiode.

The accelerometer 6 can provide time domain acceleration output signals indicative of acceleration due to movements of the user along each of three orthogonal axes (e.g., three channels of acceleration outputs). These axes can be labeled as x, y and z axes although they need not necessarily have an orientation aligned to the user's motion. For example, the device 12 can be worn on a user's wrist, and the accelerometer output signals can be indicative of the arm movements (i.e., arm swings or gait) made by the user. In other examples, the accelerometer output signals can be indicative of the foot strike of the user. Generally, the accelerations along the three axes can have mixed modes such that, for example, gait and foot strikes will appear along two or more of the axes. Additionally the acceleration artifact components within the raw PPG signals will be mixed in different proportions from those along the x, y and z acceleration axes.

In operation, the light emitter 2 can transmit a light beam to the user's skin 14, and the light beam can be reflected by the user's skin 14 and received by the light sensor 4. The light sensor 4 can convert this light into an electrical signal indicative of the intensity thereof. This electrical signal can be in analog form and can be converted into digital form by A/D converter 4a. The digital signal from the A/D converter 4a can be a time domain raw PPG heart rate signal which can be fed to the processor 8. The three outputs of the accelerometer 6 can also be converted to digital form using A/D converter 4b. While only one A/D converter 4b is illustrated in FIG. 1, it is understood that an A/D converter can be provided for each of the three x, y and z axes or alternately, a single A/D may be used to sequentially convert the acceleration signals from the three axes. The processor 8 can receive the digitized PPG signal from the light sensor 4 and the digitized accelerometer output signals from the accelerometer 6, and can process these signals to provide a heart rate (HR) output signal to the I/O unit 10. The I/O unit 10 can take the form of one or more of a storage device, a visual display, an audible annunciator, a touch screen integrated with device 12, or other output indicator. The I/O unit 10 can, under program control from the processor 8, provide historical information in visual (numeric, tabular, graphic) or audible (synthesized voice or tone) form of the detected heart rate over a period of time. As one non-limiting example, a visual graph can be displayed showing the heart rate calculated for each five minutes during a prior fixed time interval (e.g., one hour) or after an exercise period has been completed as determined by an indication thereof from the user. The I/O unit 10 can also provide, under control of the processor 8, average heart rate information or statistical information of the heat rate over a prior time period or periods. As a further example, the I/O unit 10 can provide current heart rate values as "real time" or instantaneous heart rate values displayed to the user periodically (e.g., every second) during the course of an ongoing exercise program.

The I/O unit 10 can be coupled to one or more of remote unit 18, touch screen 20 and microphone/speaker 22 or other device via wired or wireless communication links 24. The remote unit 18 can be a smart phone or other I/O device conveniently carried or worn by the user, or can be a distant computer or data server such as the user's home computer or the user's cloud storage service. The I/O unit 10 can receive input from the remote unit 18 or can receive input from the user by means of the touch screen 20 and/or the microphone/speaker 22.

Figure 2:
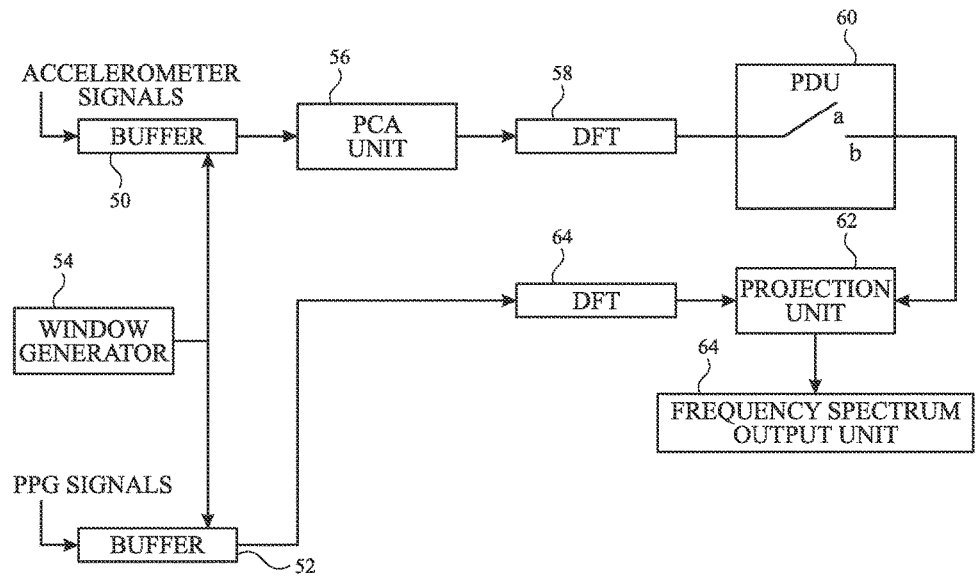
FIG. 2 is an overall flow diagram showing the data flow and computation steps used in determining the heart rate and in accordance with various disclosed examples.

FIG. 2 illustrates an exemplary flow or block diagram of functional units that can be contained within or controlled by the processor 8 of FIG. 1. The functional units can be implemented as discrete hardware units such as, for example, digital signal processors (DSP), application specific integrated circuits (ASIC), field programmable logic arrays (FPGA), or the like. The functional units can be combined into one or more interconnected devices. Alternatively, the functional units can be implemented in the form of software or firmware configured to operate a programmable processor. Further, the functional units can be a combination of discrete hardware, software and firmware.

FIG. 2 illustrates a window generator 54, buffers 50 and 52, Fourier transform unit 58 labeled DFT for discrete Fourier transform (implemented for example by a fast Fourier transform FFT), periodic determination unit (PDU) 60, projection unit 62, Fourier transform unit 64 and frequency spectrum output unit 64. The function of these units will be described below in connection with various waveforms illustrated in FIGS. 3, 4A-4C, 5A-5C, 6A-6C, 7A-7C, 8A-8C and 9.

It should be understood that additional functional units can be included, such as time-domain and/or frequency domain filter units, other signal-processing units, or timing and control units. For example, a filter unit can receive the raw time domain PPG signals including components indicative of a user's heart rate and motion artifact components. The filter unit can, for example, be a third order band-pass filter having a band-pass of 0.5-8 Hz corresponding to 30-480 bpm (beats per minute), or any other range of expected heart rate frequencies. The filter unit can remove signals that do not have frequency components that fall within or near the range expected for heart rate monitoring under various expected user conditions or activity levels.

Returning to the block diagram illustrated in FIG. 2, window generator 54 can generate windowed time domain raw PPG and acceleration signals. A sampling window can be established to assemble or concatenate a fixed number of raw PPG and acceleration signal samples that can be processed by the FDP algorithm. In some examples, an eight second window of raw PPG and acceleration signals (e.g., from time t=0 to t=8) can be utilized. Although described here as an eight second window, the window can be dynamically adjusted as described below in connection with FIGS. 13 and 14. The dynamic adjustment may, for example, adjust the window duration to be between 4-20 seconds.

Additionally, the system can use a sliding window to apply the FDP algorithm to samples from overlapping windows. The spacing between the overlapping windows can be 1-3 seconds in some examples (in other examples the spacing can be smaller or larger), but the example that follows will assume one second spacing. For example, a first window can look at data from the raw PPG and accelerometer samples from time t=0 to t=8 and a second window can look at data from time t=1 to t=9. In other words, after applying the FDP algorithm to the first window, the system can discard or exclude the first second's worth of data (e.g., samples from time t=0 to t=1) and can apply the FDP algorithm to the second window including 7 seconds of data from the first window in addition to data from then next second in time (e.g., 1024 samples from time t=1 to t=9). The process can be repeated such that the FDP algorithm can be applied with respect to each window (hence the sliding window). A sliding window can provide the benefit of having sufficient data to predict heart rate, but also providing an output every second, for example. Additionally, sequential outputs can be based on overlapping input samples (i.e., not independent of one another) such that the outputs are likely to be unaffected by short instantaneous changes in heart rate or noise.

Window generator 54 can utilize the two buffers 50 and 52. Buffers 50 and 52 can be first-in first-out (FIFO) buffers configured to receive time domain signal samples from the raw PPG sensor and the time domain signals from the accelerometer sensors sampled by A/D converters 4a and 4b respectively. For example, A/D converters 4a and 4b can have a sampling frequency of 128 Hz, although other sampling rates are possible. A 128 Hz sampling rate can produce 1024 samples for an 8 second window for each of the raw PPG and accelerometer signals. Buffers 50 and 52 respectively can supply the appropriate quantity of raw PPG and accelerometer signal samples for additional processing. In some examples, the buffers 50 and 52 can be controlled by a timing and control unit (not shown). While only one block for buffer 50 is illustrated, it is understood that three buffers may be employed, one for each of the x, y and z acceleration signals. A single window generator (e.g., 54) may be used to control all three acceleration buffers (as well as the PPG buffer 52).

Window generator 54 can generate a function which can be multiplied with the signals at the output of the buffers 50 and 52 to generate a windowing function so that the FDP process can operate on a fixed number of samples. In some examples, the windowing function can be a unit step function such that all portions of the signal outside the window of interest can be multiplied by zero and the portions of the signal inside the window of interest can be multiplied by 1. Using a unit step function, however, can cause significant distortion due to the abrupt change at the edges when converting to the frequency domain. Alternatively, rather than using the unit step function applied by the window generator 54, the buffers 50 and 52 can be controlled to output data corresponding to the window of interest (i.e. exactly 1024 data samples for each of the raw PPG and acceleration signals assuming an 8 second window and a 128 Hz sampling rate). In some examples, the size of the window may be dynamically adjusted. The window generator is explained in more detailed in a U.S. application entitled Harmonic Template Classifier, Attorney Docket Number 10684-31206.00 by James M. Silva, assigned to the same assignee as herein and filed concurrently herewith, the whole of the contents of which are incorporated by reference.

FIG. 2 utilizes a PCA unit 56. The PCA is essentially a statistical procedure using an orthogonal transform to convert possibly correlated values into a set of uncorrelated (or substantially uncorrelated) variables along principal components. The transform can be defined such that the largest possible variance of the variables occurs along the first principal axis (or component), and next highest variance occurs along the second principal axis (or component) and so forth. The results of the PCA can be component scores which can be transformed variable values corresponding to a particular data point. The PCA can also be characterized as an eigenvector-based multivariate analysis. The PCA can reveal an internal structure of a data set in a way that best explains the variance of the data. If one visualizes a multivariate data set with one axis per variable, the PCA can produce a lower dimensional picture which may be considered a projection of the object when viewed from this lower dimensional space. This projection can be is achieved using only the first few principal components so that the dimensionality of the data set is reduced. The PCA may be carried out, for example, by using MATLAB (MathWorks, Inc, Natick Mass., USA) software within Statistical Toolbox/ Multivariate Data Analysis/Principal Component Analysis (PCA) and Canonical Correlation.

The principal component analysis unit 56 of FIG. 2 can perform a principal component analysis on the time domain x, y, z acceleration signals to obtain time domain acceleration signals along a different coordinate system referred to as principal components axes PC1, PC2 and PC3. Exemplary time domain x, y and z acceleration signals are shown in FIGS. 4A, 4B and 4C respectively. When these time domain x, y and z acceleration signals are passed through the PCA unit 56, the resulting acceleration principal component scores are shown in FIGS. 5A, 5B and 5c respectively. Generally, and as may be seen by comparing the amplitudes of FIG. 5C with those of FIGS. 5A and 5B, the components along the PC3 axis can be minimal and noise-like. Thus, the PCA analysis reduces the dimensionality of the acceleration signals from three axes to two axes.

In more detail, in examining FIGS. 4A-4C, it may be seen that mixed periodic modes can occur along each of the three x, y and z axes. This is borne out by the clear periodic motions along each of the three axes of FIGS. 4A-4C, and the complexity of these waveforms is indicative of the mixed modes of the motion components as measured by the accelerometer. It is further noted that the amplitude of the signals of FIG. 4C are smaller than those of FIGS. 4A, 4B, and this results from the fact that foot strike and arm swing motions (the major contributors to the acceleration signals) are generally located in a plane (two dimensions as opposed to three). Of course, the labeling of the axes is arbitrary and has no a priori relationship with the device 14 orientation, and the designations of x, y and z are chosen for simplicity.

As compared with FIGS. 4A-4C, the principal component waveforms of FIGS. 5A-5C show the desired modal separation and resulting simplicity characteristic of the PCA algorithm. The largest amplitude peaks among the three waveforms of FIGS. 5A-5C are the peaks of PC1 in FIG. 5A. The PC1 peaks are also the most clearly defined, and can correspond to the foot strike acceleration artifact associated, for example, with a user walking, jogging or running. The PC2 peaks in FIG. 5B are periodic but much smaller in amplitude and less defined that those of the peaks of PC1. These PC2 peaks can correspond to the arm swing (or gait) of a user. The waveform of PC3 shown in FIG. 5C does not present defined periodic peaks, and this waveform looks largely like noise and is thus can be ignored. The use of the two principal components PC1 and PC2 instead of the original three acceleration axes, x, y and z demonstrates the characteristic of the PCA in reducing the dimensionality of the problem.

It is pointed out that the magnitudes of the ordinates of the graphs of FIGS. 3, 4A-4C and 5A-5C are all arbitrary units sometimes referred to as DN (digital numbers). However, the scaling is the same for FIGS. 4A-4C so the magnitude of these waveforms may be compared to one another. Likewise the scaling is the same for FIGS. 5A-5C so the magnitude of these waveforms may be compared to one another.

In reference to FIG. 2, the outputs of the PCA unit 56 can provide time domain outputs along each of the three principal axes PC1, PC2 and PC3 as shown in FIGS. 5A-5C described above. In software implementations, the principal component outputs maybe provided at essentially the same time to provide the time domain waveforms of FIGS. 5A-5C, and then transformed into the frequency domain via a FFT to produce the FD outputs as shown in FIGS. 7A-7C, respectively. The frequency content of FIGS. 7A-7C can be important. The amplitudes of these FIGS. 7A-7C have been normalized (to have power level of 1 summed over all peaks) so the amplitudes can't be directly compared one to the other. An amplitude comparison (in the time domain) may be seen from FIGS. 5A-5C. FIG. 7A shows a single well-defined peak at a frequency of 120 bpm corresponding to a foot strike rate, for example. FIG. 7B shows a single well-defined peak at a frequency of 60 bpm corresponding to the user's arm swing or gait for example. Each of FIGS. 7A and 7B has only a single well defined peak. Thus, there is a clear separation of the two frequency components of acceleration along the PC1 and PC2 axes respectively, as contrasted to the mixed modes of the x, y acceleration signals shown in FIG. 6B.

Figure 6A:
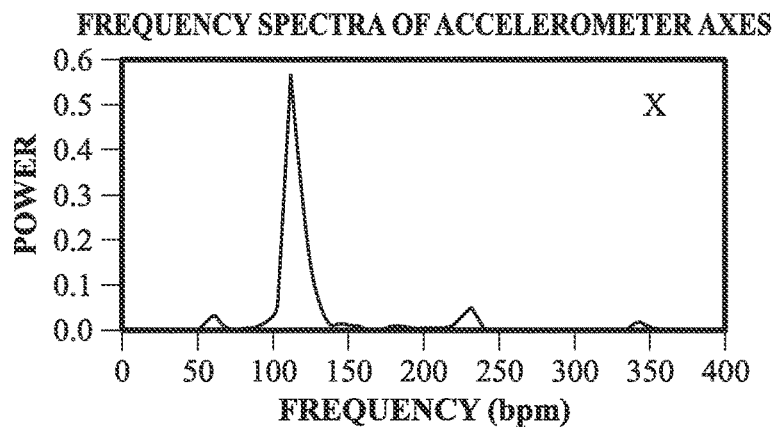
FIGS. 6A-6C illustrate respectively x, y, and z frequency domain representations of the acceleration signals of FIGS. 4A-4C according to examples of the disclosure.
Figure 6B:
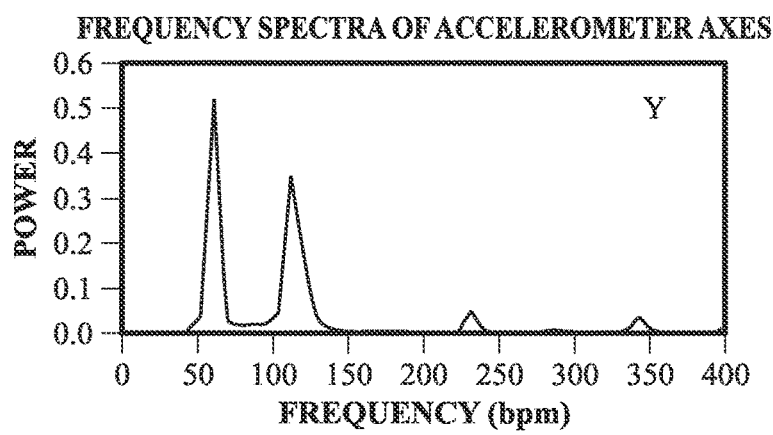
Figure 6C:
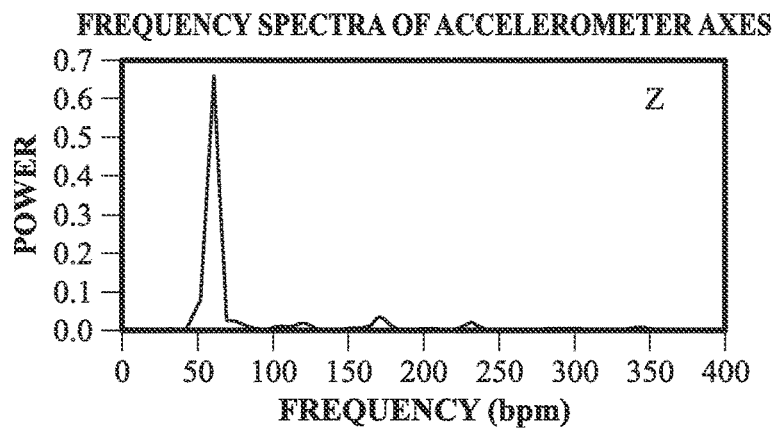
Figure 7A:
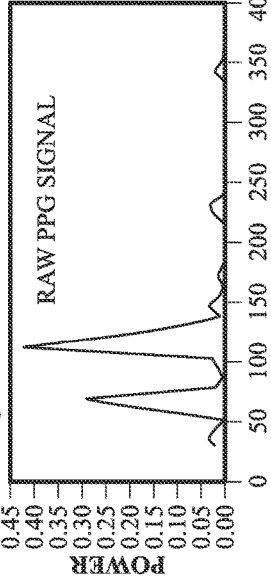
FIGS. 7A-7C illustrate, respectively principal components PC1, PC2 and PC3 frequency domain representations of the acceleration signals of FIGS. 5A-5C according to examples of the disclosure.
Figure 7B:
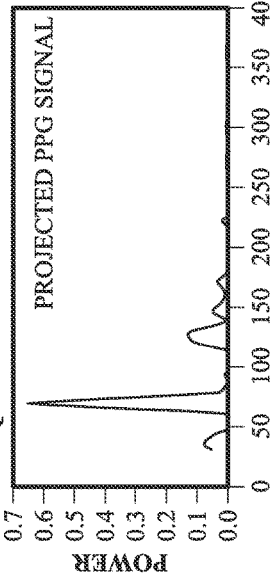
Figure 7C:
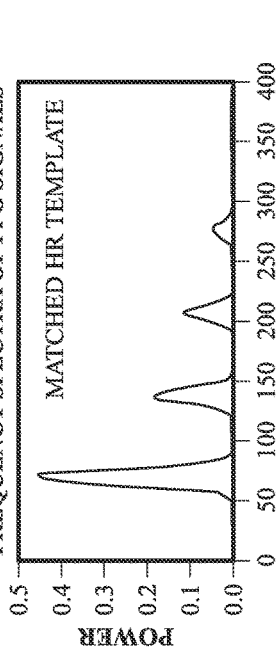

For comparison, the FD waveforms for the time domain x, y and z acceleration signals of FIGS. 4A-4C from the accelerometer are shown in FIGS. 6A-6C. While these waveforms are not utilized in the FDP algorithm, they are presented as a point of interest to show the usefulness of the PCA technique for the HR determination. While FIG. 6A is nearly the same as FIG. 7A, FIG. 6B shows mixed modes of acceleration as compared with FIG. 7B. The ability of the PCA to select coordinate axes that essentially separates out the acceleration modes such that PC1 and PC2 have only a single frequency mode permits one to individually scale the PC1 and PC2 waveforms to remove the motion artifact from the FD raw PPG signal as explained more fully below.

It is noted that the amplitudes of the signals in FIGS. 6A-6C, 7A-7C and 8A-8C are all normalized and therefore it is not meaningful to compare amplitudes among these figures.

The Fourier transform units 58 and 64 can implement an algorithm to convert time domain signals into frequency domain signals (e.g., using a discrete Fourier transform (DFT)). In some examples, the conversion algorithm can be the efficient fast Fourier transform (FFT), although other algorithms can be used. The FFT for both Fourier transform units 58 and 64 can, for example, be carried out by the same hardware, firmware and/or software and can be computed in parallel or can be time multiplexed to receive the windowed time domain PPG and principal component acceleration signals. In some cases, the FFT can be performed by existing dedicated hardware or firmware. The output of the Fourier transform units 58 and 64 can be real value outputs indicative of the magnitudes (and phases) of the frequency coefficients for the raw PPG and principal component acceleration signals during the window of interest.

The FD PC1 and PC2 acceleration signals (the FD acceleration signal waveforms along the PC1 and PC2 axes) can be are fed to the periodic determination unit (PDU) 60 to determine if they are periodic or non-periodic. Periodic movement can be characterized by well-defined peaks in the PC1, PC2 waveforms such as shown, for example in FIGS. 7A and 7B. In some examples, the amount of power present in the peaks (i.e., peaks above a first or peak threshold) as compared to the non-peaks is compared to a second or power threshold. If the amount of power present in the peaks exceeds the second or power threshold, then the motion can be considered periodic and the FD PC1, PC2 acceleration signals can be passed on to projection unit 62 via the "b" positon of a switch contained within the PDU 60. If the motion is determined to be non-periodic, the switch of the PDU 60 cam be set to the "a" positon and the data can be treated as noise and ignored.

Figure 8A:
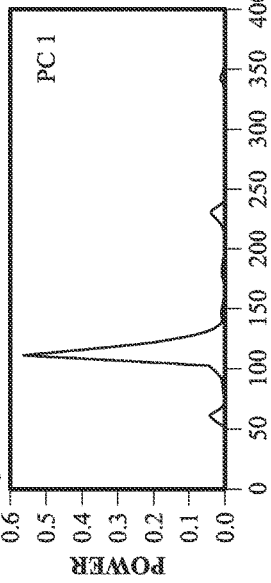
FIG. 8A illustrates the frequency domain representation of the raw PPG signals according to examples of the disclosure.

Returning once again to FIG. 2, projection unit 62 can receive the FD PC1 and PC2 acceleration signals form the PDU 60. The time domain raw PPG signals are shown in FIG. 3. The raw PPG signals can be fed to the A/D converter 4a and can be concatenated by the window generator 54 and buffer 52 and fed to the Fourier transform unit 64 to supply FD raw PPG signals to the projection unit 62. Thus, projection unit 62 can receive the FD PC1 and PC2 acceleration signals as shown in FIGS. 7A and 7B as well as the FD raw PPG signals as shown in FIG. 8A. The function of the projection unit 62 can be to remove as much as possible the FD acceleration artifact frequency components PC1 (FIG. 7A) and PC2 (FIG. 7B) from the FD raw PPG signal (FIG. 8A). In accordance with some examples of the disclosure, the FD PC1 and PC2 acceleration signals can be scaled and fitted to the FD raw PPG signals in a best fit algorithm such as a least squares fit, as a non-limiting example. Thus, the FD raw PPG signal may be approximated by A(PC1)+B(PC2), where A and B are scale factors to be determined by the best fit algorithm. Finding the scale factors may be done by successive numeric approximation techniques. The scale factors can be chosen to yield the smallest residual value obtained after subtracting the scaled sum A(PC1)+B(PC2) from the FD raw PPG signal waveform. In effect the acceleration artifacts are projected out (subtracted from) the FD raw PPG signal waveform to produce a substantially acceleration artifact-free "projected PPG" signal waveform as shown in FIG. 8B.

The FD PC1 and PC2 acceleration signal values can be largely uncorrelated and the selection of the scale factors A and B may be done individually. That is, PC1 can be representative of the single acceleration artifact at 110 bpm (corresponding to foot strike), and PC2 can be representative of the single acceleration artifact at 60 bpm (corresponding to arm swing); and the two modes are not mixed in either PC1 or PC2. If the two modes were mixed, then subtraction of the scaled sum A(PC1)+B(PC2) would yield a higher residual amount than if they were not mixed. If one did not perform the PCA, and one just used the FD acceleration signals x, y of FIGS. 6A-6B, one would not be able to determine or scale each motion (foot strike, arm swing) separately because the acceleration modes can be mixed. Complicating matters, the acceleration modes can be mixed in different proportions in the FD raw PPG waveform (FIG. 8A) than they are in the FD x and y acceleration waveforms (FIGS. 6A and 6B). An advantage of doing the PCA can be that the PC1 and PC2 data can often be uncorrelated (or largely uncorrelated), especially in acceleration applications where the acceleration motion is taking place in a plane thus minimizing the PC3 contributions. The single first frequency characteristic of PC1 and single second (different) frequency characteristic of PC2 may permit one to separately select the scale factors A and B. Any choice of these scale factors can be usable to remove at least some of the acceleration artifacts occurring at these same first and second frequencies in the FD raw PPG signal waveforms of FIG. 8A. The best fit algorithm (e.g., least squares fit) can permit one to select the A and B scale factors that minimize the residual amount after subtraction.

Figure 8B:
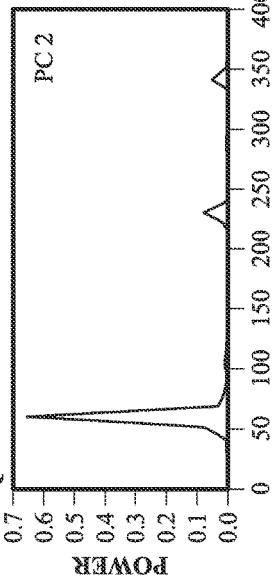
FIG. 8B illustrates the projected PPG signals in the frequency domain corresponding to the raw PPG signals of FIG. 8A after compensating for motion artifacts represented by the principal component representations of FIGS. 7A-7C according to examples of the disclosure.
Figure 9:
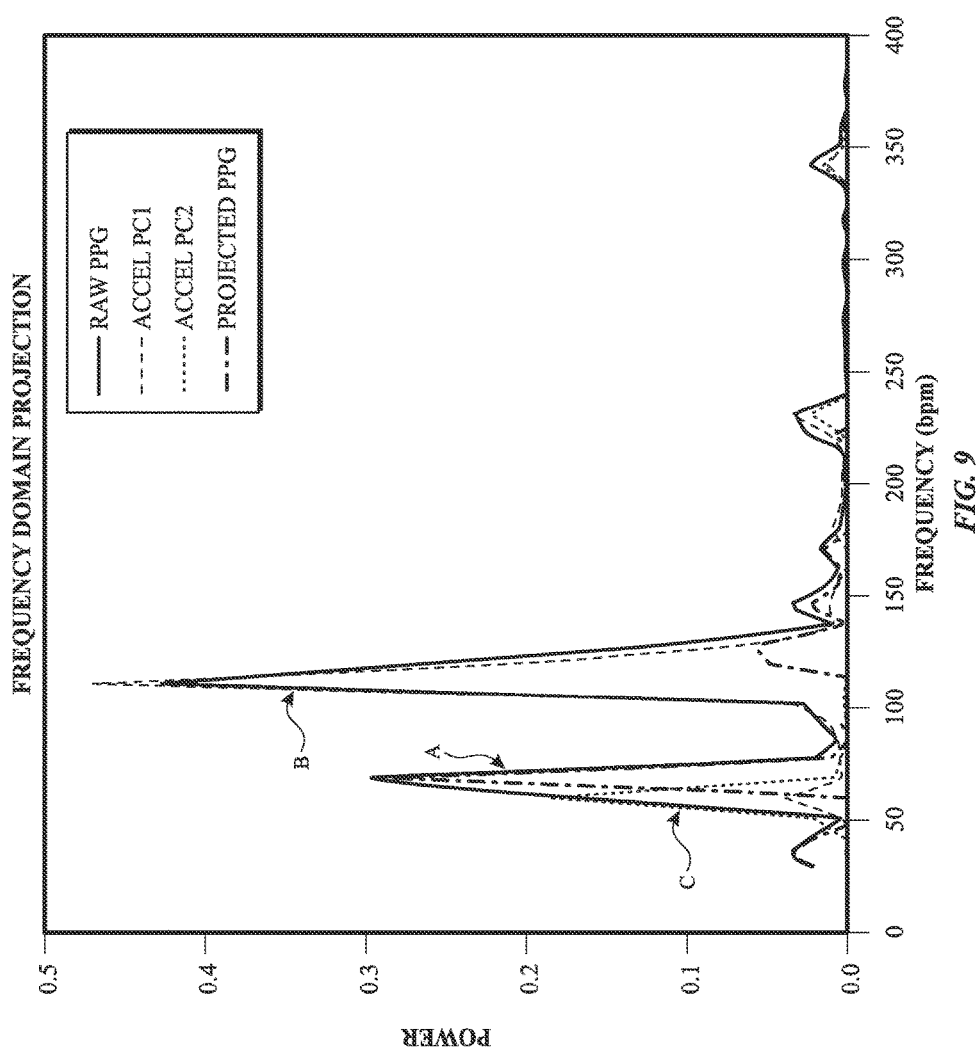
FIG. 9 illustrates a frequency domain representation of the raw PPG signal, the acceleration PC1 and PC2 signals and the projected PPG signal according to examples of the disclosure.

FIG. 9 is an illustration of the FD raw PPG waveform of FIG. 8A shown by the heavy solid line; the FD PC1 acceleration waveform of FIG. 7A shown by the dashed line; the FD PC2 acceleration waveform of FIG. 7B shown by the dotted line; and the projected PPG waveform of FIG. 8B shown by the heavy dashed-dotted line. In region labeled "A" the FD raw PPG waveform and the projected PPG waveform overlap. In the region labeled "B" the FD raw PPG waveform and the FD PC1 acceleration waveform overlap. In the region labeled "C", the FD raw PPB waveform and the FD PC2 acceleration waveform overlap. The FD PC1 and PC2 acceleration waveforms have been scaled per a best fit algorithm as discussed above such that their scaled sum, A(PC1)+B(PC2) yields a minimal residual value after being subtracted from the FD raw PPG signal waveform. (Any negative values resulting from the subtraction are set to zero). In examining FIG. 9, it is apparent that the FD raw PPG waveform has two large peaks whereas the projected PPG has only a single dominant peak at 70 bpm which in fact is not centered at the larger of the FD raw PPG peaks. The dominant projected PPG peak is much narrower and well defined than the smaller FD raw PPG waveform peak (leftmost peak of the FD raw PPG waveform), and presents an unambiguous representation of the desired HR signal frequency. In effect, removal of the FD PC2 acceleration peak at 60 bpm from the FD raw PPG waveform reveals the HR peak centered at 70 bpm. It is noted that the second largest peak of the projected PPG waveform corresponds to a first harmonic (centered at 120 bpm) of the gait (arm swing) frequency of 60 bpm. The peak is an imperfect subtraction of the motion artifact. The third peak of the projected PPG waveform is the first harmonic (at 140 bpm) of the HR signal.

The output of the projection unit 62 of FIG. 2 can be fed to frequency spectrum output unit 64 which can select the frequency corresponding to the maximum peak of the projected PPG waveform and can provide the same as an output to the user and/or for storage for later retrieval.

Figure 8C:
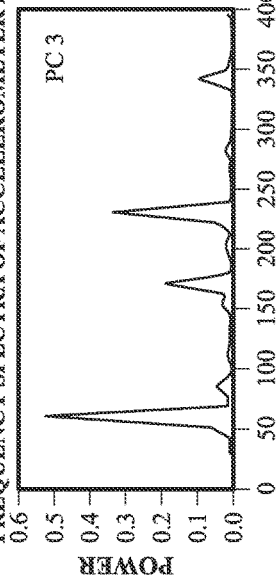
FIG. 8C illustrates a frequency domain template which matches the frequency spectrum of the projected PPG signal of FIG. 8B according to examples of the disclosure.
Figure 10:
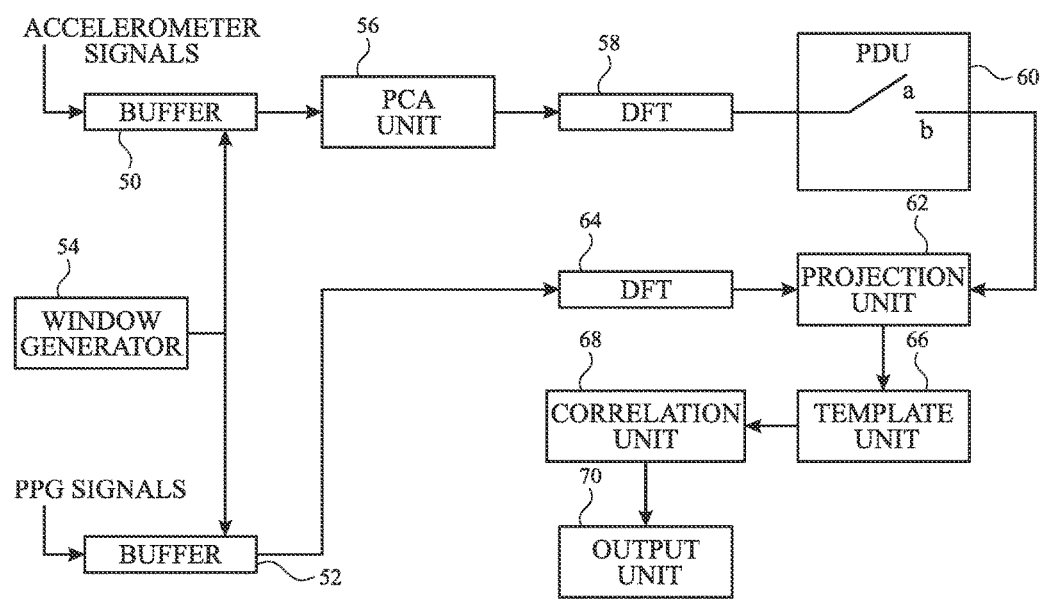
FIG. 10 shows an overall flow diagram of the frequency domain projection analysis similar to FIG. 1 and employed to determine heart rate according to examples of the disclosure utilizing templates.
Figure 11:
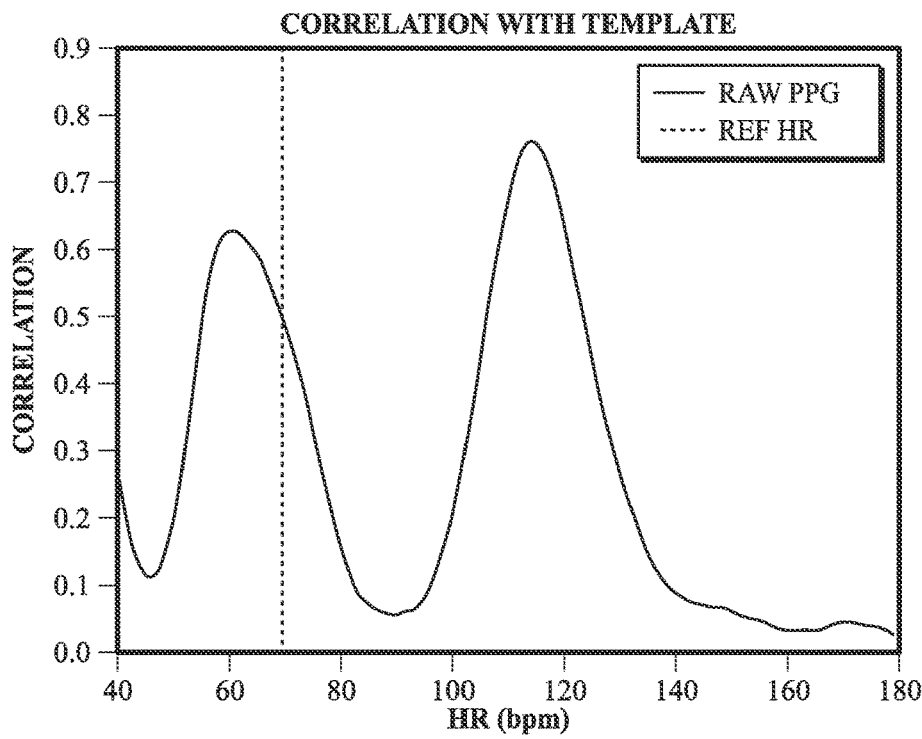
FIG. 11 shows a correlation plot of the raw PPG signal with a pre-stored HR template according to examples of the disclosure utilizing templates.

FIG. 10 is a flow or block diagram similar to that of FIG. 2 and common elements are commonly labeled. Additional units of FIG. 10 include the template unit 66, correlation unit 68 and output unit 70 (which can be similar to the frequency spectrum output unit 64). The template unit 66 can store fundamental and harmonic waveforms in the form of templates for each possible HR that may be observed. An exemplary template is shown in FIG. 8C for a HR of 70 bpm for comparison with the projected PPG signal waveform of FIG. 8b. Templates may be stored for each HR value between 30-220 bpm as a representative range. The template unit 66 can correlate the waveforms of the stored templates with an input waveform. By way of example, the correlation unit 66 may correlate the stored templates with the FD raw PPG signal from the Fourier transformation unit 64 and the results of such a correlation are shown in FIG. 11. This correlation plot shows that there are two strong correlations, one occurring at approximately 60 bpm and having a wide spread, and the other occurring at a frequency of approximately 120 bpm. Both peak correlations are approximately the same value and neither one is sufficiently close to the reference HR of 70 bpm as shown by the dotted line in FIG. 11.

Figure 12:
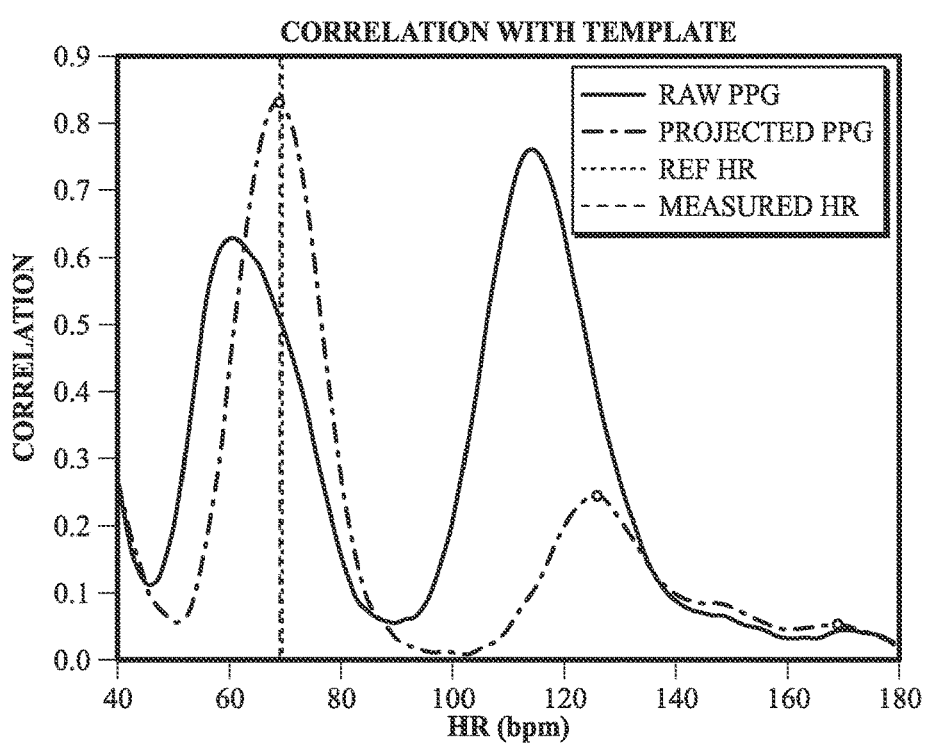
FIG. 12 shows a correlation plot of the raw PPG signal similar to FIG. 11 but also including a correlation plot of the projected PPG signal according to examples of the disclosure.

FIG. 12 shows the template matching process for both the FD raw PPG signal (as in FIG. 11) and the FD projected PPG signal from the projection unit 62. The template unit 66 can correlate this FD projected PPG signal waveform with each stored template waveform for each of the possible HR values. The resulting correlation curve is shown by the heavy dashed-dotted line in FIG. 12. It may be appreciated that the correlation for the FD projected PPG signal waveform shows a dominant peak very close to the reference HR of 70 bpm. The dominant peak of the correlation plot of the FD projected PPG signal waveform is much higher (larger correlation) than any other correlation peak unlike the two closely matched correlation peaks of the FD raw PPG signal waveforms represented by the heavy solid lines in FIGS. 11 and 12. Thus, there are fewer "distractors" (reasonable alternative choices) in choosing the measured HR as the highest correlation peak of the FD projected PPG signal waveform. The output unit 70 of FIG. 10 can select the center of the dominant peak in the FD projected PPG signal waveforms as the "measured" value of the HR and can provide this HR data to the user and/or can store the same for later display or processing. The associated confidence level may also be output and/or stored. The measured HR value taken from the peak of the correlation curve for the FD projected PPG signal waveform is shown by the dashed line in FIG. 12, and this measured value is seen to be substantially the same as the reference HR value shown by the dotted line in FIG. 12, namely 70 bpm.

Figure 13:
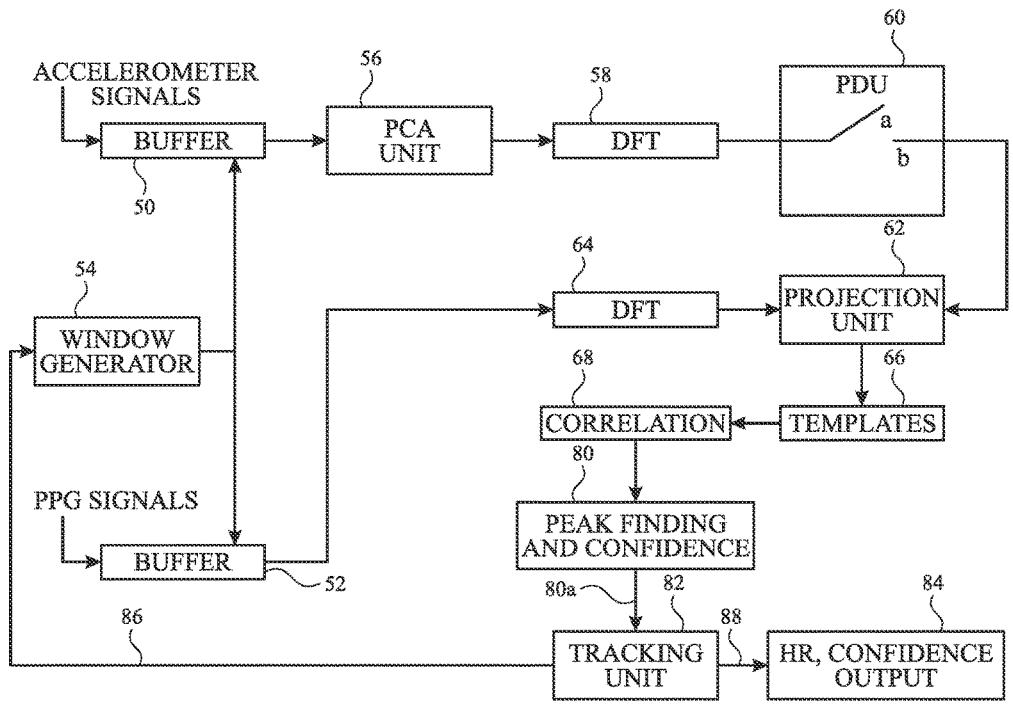
FIG. 13 shows an overall flow diagram of the frequency domain projection analysis similar to FIG. 10 and employed to determine heart rate according to examples of the disclosure utilizing confidence determination and tracking.

FIG. 13 is a flow or block diagram similar to that of FIG. 10 and common elements are commonly labeled. Additionally units of FIG. 13 include a peak finding and confidence unit 80, a tracking unit 82 a HR and confidence and output unit 84. The tracking peak finding and confidence unit 80 can be connected to the tracking unit 82 along line 80a, and the tracking unit 82 can be connected to the window generator 54 along a line 86. The peak finding and confidence unit 80 can obtain the HR peak from the correlation plots (FIG. 12) produced by the correlation unit 68 and can assign a confidence level to the selected HR peak. The confidence level may be computed as a scaled version of the correlation value at each peak, divided by a norm of the full correlation plot. Non-limitng example of a norm would be the square root of the sum of squares, or the sum of absolute values. In this way, a penalty can be imposed for low correlations as well as correlation plots with many peaks. The HR peak values and their associated confidence levels can be output to the tracking unit 82 along line 80a. The tracking unit 82 can track prior and current values of the HR and their associated confidence values and can pick the HR with the largest confidence, and can output the selected HR and its confidence level the "HR, confidence output unit" 84 for display and/or storage for later processing.

Figure 14:
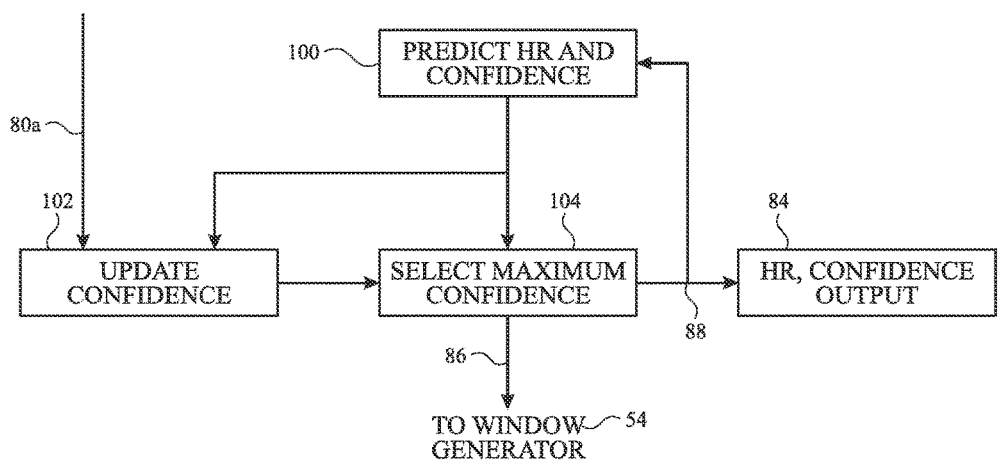
FIG. 14 shows a flow diagram of the tracking unit of FIG. 13.

The tracking unit 82 is shown in more detail in FIG. 14 and is seen to comprise a predict HR and confidence unit 100, an update confidence unit 102, a select maximum confidence unit 104, and the HR, confidence output 84 (of FIG. 13). The predict HR and confidence unit 100 can store at least one or more previously determined values of HR and associated confidences and can utilize at least the most recently previously stored HR and confidence value in the prediction process. An assumption underlying the prediction is that the current HR will be predicted to be the same as the most recently previously determined HR but the confidence level associated with that HR will be revised to be smaller. The longer the time interval between the current HR value and the most recently previously determined (stored) HR value, the smaller the confidence of the most recently previously determined HR value. The prior (most recently previously determined) HR value and its revised confidence level can be fed to the update confidence unit 102 from the predict HR and confidence unit 100. The update confidence unit 102 can receive both the new HR and associated confidence level, and the prior (most recently previously determined) HR and its revised confidence level. The update confidence unit 102 can reduce the confidence of the new HR peak value based on how far away the new peak is from the prior HR value. The assumption is that the HR value should not change too much form one second to the next (assuming a one second spacing between overlapping windows). The select maximum confidence unit 104 can select the peak with the highest confidence among the new and prior (most recently previously determined) values to be the new measured HR value, and can output this value with its associated confidence to the HR, confidence output unit 84. In other examples, acceleration signals output, for example, from the buffer 50 can be fed to and monitored by the predict HR and confidence unit 100, and information about the current state of acceleration may be used in deciding the how to modify the past HR value and/or how to modify the prior confidence level associated with the past HR value. For example, if the user's acceleration signals showed a marketed increase in signal frequency, triggered, for example, by the user going from a walking state to a jogging state, the increased acceleration signal frequency could be used to change how one treats the past (stored) HR values. In the case of such an increase in acceleration frequency, instead of using the same HR value in the past as the predicted value, the past (stored) HR value can be increased by one or more bpm depending upon the amount of increase in the acceleration frequency. Alternately, or additionally, the confidence level associated with the past (stored) HR may be further reduced (reduced above that which would otherwise be reduced without the additional acceleration data) in view of the increased frequency of the acceleration data. If the acceleration data showed a marked decrease in frequency, as triggered, for example, by the user going from a jogging state to a walking state, the decreased acceleration signal frequency could be used by the predict HR and confidence unit 100 to predict a HR one or more bpm lower than the past (stored) HR. Alternately, or additionally, the confidence level associated with the past (stored) HR may be further reduced (reduced above that which would otherwise be reduced without the additional acceleration data) in view of the decreased in frequency of the acceleration data.

An output of the select maximum confidence unit 104 can also be provided along line 86 to the window generator 54 to dynamically adjust the size of the window. Several factors can contribute to determining the sampling window size. For example, a shorter sampling window can result in a heart rate output (e.g., average heart rate over the course of the window) that more strongly correlates to the actual heart rate conditions at the time (i.e., output can be less impacted by changes in heart rate that occurred earlier or later in time). In contrast, a larger sampling window can result in additional samples of the PPG signal that improve the ability to detect the heart rate signal (e.g., at 60 bpm an 8 second window can contain 8 samples of the heart rate signal). For example, if the prior HR measurement had a higher confidence than the new HR value (as determined by the select maximum confidence unit 104), the implication is that the current data may not be as good as the prior data. In such cases, the sampling window can be enlarged which can give better frequency resolution of the PPG signal for the next window samples. A disadvantage for extending the window can be that it can introduce more time delay into the system, because more data may be needed to produce an answer. Time delay can be introduced by averaging or smoothing over the window length. The longer the window length the less able the system is able to track small variations in HR, but the use of the longer window can improve accuracy in those cases where the signal is hard to find. On the other hand, if new data was better than old (predicted), the sampling window can be shortened under the theory that the current data is good, and a shorter sampling window can allow for the system to be more responsive to small changes in HR.

The dynamic adjustment of the size of the window of window generator (and buffer) is not dependent upon the existence or the details of the data processing in units 56, 58, 64, 60, 62, 66 and 68. Generally the dynamic adjustment may be implemented when data values from a window are processed and stored such that prior processed samples are available for comparison to currently measured samples. In some examples, confidence values are associated with the stored processed samples and the currently measured samples. In general the dynamic adjustment involves a device for adjusting a data sampling window size for processing data and includes a first sensor for accumulating the data during the sampling window; processing circuitry capable of determining a current value associated with the accumulated data; and comparing the determined current value with a previously determined value of the data and adjusting the data sampling window size depending on the results of the comparison.

While the description of FIGS. 2, 10, 13 and 14 has been made largely with respect to "units" generally indicative of hardware structures, it is pointed out that these figures may also be representative of block diagrams where the functional operation of each "unit" is one or more steps of a software program executed by the processor 8 of FIG. 2. For example, in reference to FIG. 2, the software steps may be understood as storing a number of samples (buffer 50, 52) where the sample size is variable (window generator 54); performing a principal component analysis on the samples of the acceleration artifact signals (PCA unit 56); performing a Fourier transform on the principal components of the PCA (DFT 58) and also a Fourier transform of the raw PPG signals (DFT 64); determining whether the signals from the Fourier transform of the principal component analysis PC1, PC2 are periodic or non-periodic (PDU 60); projecting out or subtracting out a scaled sum of the PC1 and PC2 waveforms (A(PC1)+B(PC12)) to remove acceleration artifacts from the FD raw PPG waveform (Projection unit 62); and determining the dominant peak in the resulting projected PPG signal waveform as an indication to the user and/or for storage (frequency spectrum output unit 64). In this manner it may be understood that each of the blocks in FIGS. 2, 10, 13 and 14 may be implement as programmed steps of a programmable computer or processor.

Figure 15:
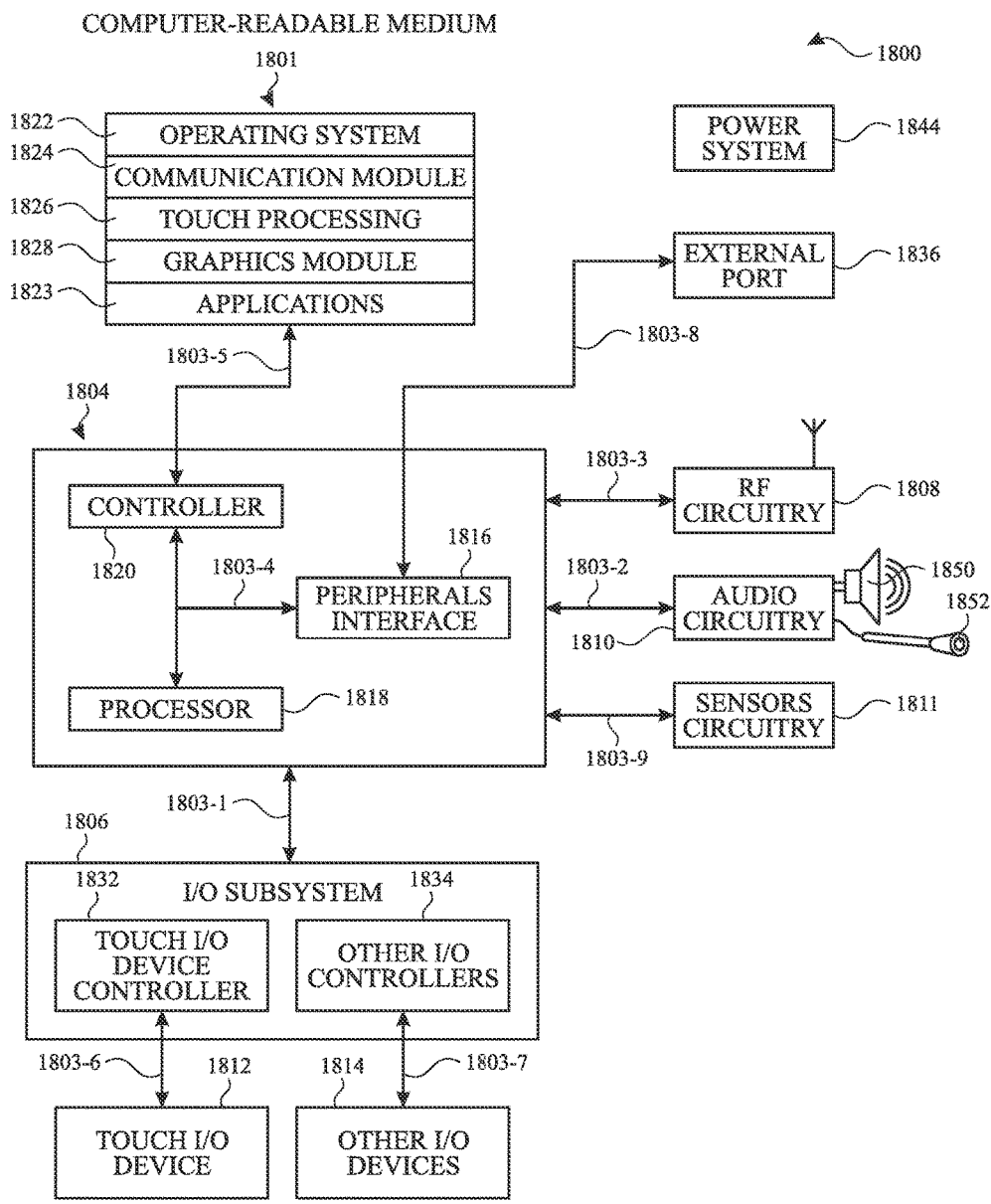
FIG. 15 illustrates a block diagram of an exemplary system architecture that can implement the frequency domain projection analysis according to examples of the disclosure.

A system architecture implementing the FDP algorithm can be included in any portable or non-portable device including but not limited to a wearable device (e.g., smart band, health band, smart watch), a communication device (e.g., mobile phone, smart phone), a multi-media device (e.g., MP3 player, TV, radio), a portable or handheld computer (e.g., tablet, netbook, laptop), a desktop computer, an All-In-One desktop, a peripheral device, or any other system or device adaptable to the inclusion of system architecture, including combinations of two or more of these types of devices. FIG. 15 illustrates a block diagram of an exemplary system architecture 1800 that can implement the FDP algorithms according to examples of the disclosure. System architecture 1800 can generally include one or more computer-readable media 1801, processing system 1804, I/O subsystem 1806, radio frequency (RF) circuitry 1808, audio circuitry 1810, and sensors circuitry 1811. These components can be coupled by one or more communication buses or signal lines 1803.

It should be understood that the exemplary architecture shown in FIG. 15 can have more or fewer components than shown, or a different configuration of components. The various components shown in FIG. 15 can be implemented in hardware, software, firmware or any combination thereof, including one or more signal processing and/or application specific integrated circuits.

RF circuitry 1808 can be used to send and receive information over a wireless link or network to one or more other devices and includes well-known circuitry for performing this function. RF circuitry 1808 and audio circuitry 1810 can be coupled to processing system 1804 via peripherals interface 1816. Interface 1816 can include various known components for establishing and maintaining communication between peripherals and processing system 1804. Audio circuitry 1810 can be coupled to audio speaker 1850 and microphone 1852 and can include known circuitry for processing voice signals received from interface 1816 to enable a user to communicate in real-time with other users. In some examples, audio circuitry 1810 can include a headphone jack (not shown). Sensors circuitry 1811 can be coupled to various sensors including, but not limited to, one or more light emitting diodes (LEDs) or other light emitters, one or more photodiodes or other light sensors, one or more photothermal sensors, a magnetometer, an accelerometer, a gyroscope, a barometer, a compass, a proximity sensor, a camera, an ambient light sensor, a thermometer, a GPS sensor, and various system sensors which can sense remaining battery life, power consumption, processor speed, CPU load, and the like.

Peripherals interface 1816 can couple the input and output peripherals of the system 1800 to one or more processor 1818 and one or more computer-readable mediums 1801 via a controller 1820. The one or more processors 1818 communicate with the one or more computer-readable media 1801 via the controller 1820. The one more computer-readable media 1801 can be any device or medium that can store code and/or data for use by the one or more processors 1818. In some examples, medium 1801 can be a non-transitory computer-readable storage medium. Medium 1801 can include a memory hierarchy, including but not limited to cache, main memory and secondary memory. The memory hierarchy can, as non-limiting examples, be implemented using any combination of RAM (e.g., SRAM, DRAM, DDRAM), ROM, FLASH, magnetic and/or optical storage devices, such as disk drives, magnetic tape, compact disks (CDs) and digital video discs (DVDs). Medium 1801 can also include a transmission medium for carrying information-bearing signals indicative of computer instructions or data (with or without a carrier wave upon which the signals can be modulated). For example, the transmission medium can include a communications network, including but not limited to the Internet (also referred to as the World Wide Web), intranet(s), Local Area Networks (LANs), Wide Local Area Networks (WLANs), Storage Area Networks (SANs), Metropolitan Area Networks (MAN) and the like.

One or more processors 1818 can run various software components stored in medium 1801 to perform various functions for system architecture 1800. In some examples, the software components can include operating system 1822, communication module (or set of instructions) 1824, touch processing module (or set of instructions) 1826, graphics module (or set of instructions) 1828, and one or more applications (or set of instructions) 1823. Each of these modules and above noted applications can correspond to a set of instructions for performing one or more functions described above and the methods described in this application (e.g., the computer-implemented methods and other information processing methods described herein). These modules (i.e., sets of instructions) need not be implemented as separate software programs, procedures or modules, and thus various subsets of these modules can be combined or otherwise re-arranged in various examples. In some examples, medium 1801 can store a subset of the modules and data structures identified above. Furthermore, medium 1801 can store additional modules and data structures not described above.

Operating system 1822 can include various procedures, sets of instructions, software components and/or drivers for controlling and managing general system tasks (e.g., memory management, storage device control, power management, etc.) and facilitates communication between various hardware and software components.

Communication module 1824 can facilitate communication with other devices over one or more external ports 1836 or via RF circuitry 1808 and can include various software components for handling data received from RF circuitry 1808 and/or external port 1836.

Graphics module 1828 can include various known software components for rendering, animating and displaying graphical objects on a display surface. In examples in which touch I/O device 1812 is a touch sensing display (e.g., touch screen), graphics module 1828 can include components for rendering, displaying, and animating objects on the touch sensing display. The touch I/O device 1812 and/or the other I/O device 1814 can comprise the I/O unit 10 of FIG. 1, and can also incorporate a UI interface permitting a use to select among programming modes of displaying heart rate data when the I/O device is incorporated into a device 12 of FIG. 1. Further, in relation to FIG. 1, the light emitter 2 and light sensor 4 can be part of the I/O device 1814, and the touch screen 20 can correspond to the touch I/O device 1812 of FIG. 15. The I/O unit 10 either integrated within device 12 or via coupling to microphone/speaker 22 can also provide audio outputs as part of the user communications corresponding to audio circuitry 1810 of FIG. 15. Microphone 1852 of FIG. 15 can correspond to the microphone/speaker unit 22 of FIG. 1.

One or more applications 1823 can include any applications installed on system 1800, including without limitation, a browser, address book, contact list, email, instant messaging, word processing, keyboard emulation, widgets, JAVA-enabled applications, encryption, digital rights management, voice recognition, voice replication, location determination capability (such as that provided by the global positioning system (GPS)), a music player, etc.

Touch processing module 1826 can include various software components for performing various tasks associated with touch I/O device 1812 including but not limited to receiving and processing touch input received from touch I/O device 1812 via touch I/O device controller 1832.

I/O subsystem 1806 can be coupled to touch I/O device 1812 and one or more other I/O devices 1814 for controlling or performing various functions. Touch I/O device 1812 can communicate with processing system 1804 via touch I/O device controller 1832, which can include various components for processing user touch input (e.g., scanning hardware). One or more other input controllers 1834 can receive/send electrical signals from/to other I/O devices 1814. Other I/O devices 1814 can include physical buttons, dials, slider switches, sticks, keyboards, touch pads, additional display screens, or any combination thereof.

If embodied as a touch screen, touch I/O device 1812 can display visual output to the user in a GUI. The visual output can include text, graphics, video, and any combination thereof. Some or all of the visual output can correspond to user-interface objects. Touch I/O device 1812 can form a touch sensing surface that accepts touch input from the user. Touch I/O device 1812 and touch screen controller 1832 (along with any associated modules and/or sets of instructions in medium 1801) can detect and track touches or near touches (and any movement or release of the touch) on touch I/O device 1812 and can convert the detected touch input into interaction with graphical objects, such as one or more user-interface objects. In the case in which device 1812 is embodied as a touch screen, the user can directly interact with graphical objects that can be displayed on the touch screen. Alternatively, in the case in which device 1812 is embodied as a touch device other than a touch screen (e.g., a touch pad), the user can indirectly interact with graphical objects that can be displayed on a separate display screen embodied as I/O device 1814.

Touch I/O device 1812 can be analogous to the multi-touch sensing surface described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1.

In examples for which touch I/O device 1812 is a touch screen, the touch screen can use liquid crystal display (LCD) technology, light emitting polymer display (LPD) technology, organic LED (OLED), or organic electro luminescence (OEL), although other display technologies can be used in other examples.

Feedback can be provided by touch I/O device 1812 based on the user's touch input as well as a state or states of what is being displayed and/or of the computing system. Feedback can be transmitted optically (e.g., light signal or displayed image), mechanically (e.g., haptic feedback, touch feedback, force feedback, or the like), electrically (e.g., electrical stimulation), olfactory, acoustically (e.g., beep or the like), or the like or any combination thereof and in a variable or non-variable manner.

System architecture 1800 can also include power system 1844 for powering the various hardware components and can include a power management system, one or more power sources, a recharging system, a power failure detection circuit, a power converter or inverter, a power status indicator and any other components typically associated with the generation, management and distribution of power in portable devices.

In some examples, peripherals interface 1816, one or more processors 1818, and memory controller 1820 of the processing system 1804 can be implemented on a single chip. In some other examples, they can be implemented on separate chips.

Therefore, according to the above, some examples of the disclosure are directed to a device for predicting heart rate (HR), having a first sensor configured to generate raw HR signals; a second sensor configured to generate acceleration signals along at least a first direction; and processing circuitry. The processing circuitry is capable of generating a frequency domain (FD) representation of the raw HR signals to provide a FD raw HR signal waveform; generating a FD representation of the acceleration signals to provide a FD acceleration signal waveform along the first direction; scaling a peak in the FD acceleration signal waveform at a first frequency to represent a peak at the same first frequency in the FD raw HR signal waveform; subtracting the scaled peak of the FD acceleration signal waveform from the FD raw HR signal waveform to obtain a FD projected HR signal waveform; selecting the frequency corresponding to the maximum peak of the FD projected HR signal waveform; and predicting a HR based on the selected frequency.

Alternative or additionally one or more of the examples disclosed above, in some examples, the processing circuitry is further capable of: correlating the FD projected HR signal waveform with a plurality of spectral heart rate templates to generate a plurality of correlation values; and predicting a heart rate based on the selected frequency and the plurality of correlation values. The processing circuitry is further capable of generating groups of raw HR signals and acceleration signals such that the FD raw HR signal waveforms and the FD acceleration signal waveforms are based on discrete Fourier transforms of the groups of raw HR signals and acceleration signals; and dynamically adjusting the size of the groups in response to at least the selected frequency and previously selected frequencies.

Disclosed examples also include a device for predicting heart rate (HR), having a first sensor configured to generate time domain raw HR signals; a second sensor configured to generate time domain acceleration signals along first, second and third directions; and processing circuitry. The processing circuitry is capable of performing a principal component analysis of the time domain acceleration signals along the first, second and third directions to provide time domain principal components acceleration waveforms of the time domain acceleration signals having scores along the principal component axes PC1 and PC2; generating a frequency domain (FD) representation of the time domain raw HR signals to provide a FD raw HR signal waveform; generating a FD representation of the time domain principal components acceleration waveforms to provide FD acceleration signal waveforms corresponding to the principal component axes PC1 and PC2 and designating the corresponding waveforms as FD PC1 acceleration signal waveforms and FD PC2 acceleration signal waveforms respectively; and utilizing the FD PC1 acceleration signal waveforms, the FD PC2 acceleration signal waveforms and the FD raw HR signal waveform to predict the HR.

The processing circuitry utilizes the FD PC1 acceleration signal waveforms, the FD PC2 acceleration signal waveforms and the FD raw HR signal waveform to predict the HR by forming a combination of the FD PC1 and FD PC2 acceleration signal waveforms; subtracting the combination of the FD PC1 and FD PC2 acceleration signal waveforms from the FD raw HR signal waveform to obtain a FD projected HR signal waveform; selecting the frequency corresponding to the maximum peak of the FD projected HR signal waveform; and edicting a HR based on the selected frequency. The first sensor may be a photoplethysmogram (PPG) sensor and the time domain raw HR signals may be time domain raw PPG signals. The combination of the FD PC1 and FD PC2 acceleration signal waveforms may take the form of A{FD PC1 acceleration signal waveform}+ B{FD PC2 acceleration signal waveform} respectively where A and B are scale factors. The scale factors A and B may be determined by a successive approximation algorithm such as to minimize a residual value. The processing circuitry may further be capable of generating groups of time domain raw HR signals and time domain acceleration signals such that the FD raw HR signal waveforms and the FD acceleration signal waveforms are based on discrete Fourier transforms of the groups of raw HR signals and acceleration signals; and dynamically adjusting the size of the groups in response to at least the selected frequency and previously selected frequencies.

Some examples of the disclosure also include a device for predicting heart rate (HR), having a first sensor configured to generate time domain raw HR signals; a second sensor configured to generate time domain acceleration signals along first, second and third directions; and processing circuitry. The processing circuitry may be capable of performing a principal component analysis of the time domain acceleration signals along the first, second and third directions to provide time domain principal components acceleration waveforms of the time domain acceleration signals having scores along the principal component axes PC1 and PC2; generating a frequency domain (FD) representation of the time domain raw HR signals to provide a FD raw HR signal waveform; generating a FD representation of the time domain principal components acceleration waveforms to provide FD acceleration signal waveforms corresponding to the principal component axes PC1 and PC2 and designating the corresponding waveforms as FD PC1 acceleration signal waveforms and FD PC2 acceleration signal waveforms respectively; and utilizing the FD PC1 acceleration signal waveforms, the FD PC2 acceleration signal waveforms, the FD raw HR signal waveform and a plurality of spectral heart rate templates to generate a plurality of correlation values to predict the HR.

The processing circuitry may utilize the FD PC1 acceleration signal waveforms, the FD PC2 acceleration signal waveforms, the FD raw HR signal waveform and a plurality of spectral heart rate templates to generate a plurality of correlation values to predict the HR by forming a combination of the FD PC1 and FD PC2 acceleration signal waveforms; subtracting the combination of the FD PC1 and FD PC2 acceleration signal waveforms from the FD raw HR signal waveform to obtain a FD projected HR signal waveform; correlating the FD projected HR signal waveform with the plurality of spectral heart rate templates to generate the plurality of correlation values; and predicting a heart rate based on the highest correlation value among the plurality of correlation values. The first sensor may be a photoplethysmogram (PPG) sensor and the time domain raw HR signals may be time domain raw PPG signals. The combination of the FD PC1 and FD PC2 acceleration signal waveforms may be of the form A{FD PC1 acceleration signal waveform}+ B{FD PC2 acceleration signal waveform} respectively where A and B are scale factors. The scale factors A and B are determined by a successive approximation algorithm such as to minimize a residual value. Further, the processing circuitry may be capable of generating groups of time domain raw HR signals and time domain acceleration signals such that the FD raw HR signal waveforms and the FD acceleration signal waveforms are based on discrete Fourier transforms of the groups of raw HR signals and acceleration signals; and dynamically adjusting the size of the groups in response to at least the correlation values. The processing circuitry may further be capable of dynamically adjusting the size of the groups dependent on a currently predicted HR, a previously predicted HR and correlation values associated with the currently predicted HR and the previously predicted HR.

Some examples of the disclosure are directed to a device for adjusting a data sampling window size for processing data having a first sensor for accumulating the data during the sampling window and processing circuitry. The processing circuitry may be capable of determining a current value associated with the accumulated data; comparing the determined current value with a previously determined value of the data; adjusting the data sampling window size depending on the results of the comparison. The processing circuitry may be further capable of determining a confidence level associated with the determined current and previously determined values; selecting a highest confidence level associated with the current and previously determined values; and adjusting the data sampling window size depending on the selected confidence level.

The disclosure also encompasses a method for predicting heart rate (HR), comprising generating time domain raw HR signals; generating time domain acceleration signals along first, second and third directions; performing a principal component analysis of the time domain acceleration signals along the first, second and third directions to provide time domain principal components acceleration waveforms of the time domain acceleration signals having scores along the principal component axes PC1 and PC2; generating a frequency domain (FD) representation of the time domain raw HR signals to provide a FD raw HR signal waveform; generating a FD representation of the time domain principal components acceleration waveforms to provide FD acceleration signal waveforms corresponding to the principal component axes PC1 and PC2 and designating the corresponding waveforms as FD PC1 acceleration signal waveforms and FD PC2 acceleration signal waveforms respectively; and utilizing the FD PC1 acceleration signal waveforms, the FD PC2 acceleration signal waveforms and the FD raw HR signal waveform to predict the HR. The method further involves forming a combination of the FD PC1 and FD PC2 acceleration signal waveforms; subtracting the combination of the FD PC1 and FD PC2 acceleration signal waveforms from the FD raw HR signal waveform to obtain a FD projected HR signal waveform; selecting the frequency corresponding to the maximum peak of the FD projected HR signal waveform; and predicting a HR based on the selected frequency. The time domain raw HR signals may be generated from a photoplethysmogram (PPG) sensor. The combination of the FD PC1 and FD PC2 acceleration signal waveforms may be of the form A{FD PC1 acceleration signal waveform}+B{FD PC2 acceleration signal waveform} respectively where A and B are scale factors. The scale factors A and B are determined by a successive approximation algorithm such as to minimize a residual value. The method may further comprise generating groups of time domain raw HR signals and time domain acceleration signals such that the FD raw HR signal waveforms and the FD acceleration signal waveforms are based on discrete Fourier transforms of the groups of raw HR signals and acceleration signals; and dynamically adjusting the size of the groups in response to at least the selected frequency and previously selected frequencies.

The disclosed examples also include a method for predicting heart rate (HR), comprising generating time domain raw HR signals; generating time domain acceleration signals along first, second and third directions; performing a principal component analysis of the time domain acceleration signals along the first, second and third directions to provide time domain principal components acceleration waveforms of the time domain acceleration signals having scores along the principal component axes PC1 and PC2; generating a frequency domain (FD) representation of the time domain raw HR signals to provide a FD raw HR signal waveform; generating a FD representation of the time domain principal components acceleration waveforms to provide FD acceleration signal waveforms corresponding to the principal component axes PC1 and PC2 and designating the corresponding waveforms as FD PC1 acceleration signal waveforms and FD PC2 acceleration signal waveforms respectively; and utilizing the FD PC1 acceleration signal waveforms, the FD PC2 acceleration signal waveforms, the FD raw HR signal waveform and a plurality of spectral heart rate templates to generate a plurality of correlation values to predict the HR.

The method may further comprising forming a combination of the FD PC1 and FD PC2 acceleration signal waveforms; subtracting the combination of the FD PC1 and FD PC2 acceleration signal waveforms from the FD raw HR signal waveform to obtain a FD projected HR signal waveform; correlating the FD projected HR signal waveform with the plurality of spectral heart rate templates to generate the plurality of correlation values; and predicting a heart rate based on the highest correlation value among the plurality of correlation values.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

What is claimed as new and desired to be protected by Letters Patent of the United States is:

1. A device for predicting heart rate (HR), comprising:
    a first sensor configured to generate time domain raw HR signals;
    a second sensor, distinct from the first sensor and configured to generate time domain acceleration signals along first, second and third directions; and
    processing circuitry configured for:
    performing a principal component analysis of the time domain acceleration signals to provide time domain principal components acceleration waveforms of the time domain acceleration signals having scores along the principal component axes PC1 and PC2;
    generating a frequency domain (FD) representation of the time domain raw HR signals to provide a FD raw HR signal waveform;
    generating a FD representation of the time domain principal components acceleration waveforms to provide FD acceleration signal waveforms corresponding to the principal component axes PC1 and PC2, the corresponding waveforms being FD PC1 acceleration signal waveforms and FD PC2 acceleration signal waveforms respectively; and
    utilizing the FD PC1 acceleration signal waveforms, the FD PC2 acceleration signal waveforms and the FD raw HR signal waveform to predict the HR
    wherein the processing circuitry further configured to utilize the FD PC1 acceleration signal waveforms, the FD PC2 acceleration signal waveforms and the FD raw HR signal waveform to predict the HR by:
    forming a combination of the FD PC1 and FD PC2 acceleration signal waveforms;
    subtracting the combination of the FD PC1 and FD PC2 acceleration signal waveforms from the FD raw HR signal waveform to obtain a FD projected HR signal waveform;
    selecting a frequency corresponding to the maximum peak of the FD projected HR signal waveform;
    predicting a HR based on the selected frequency; and
    displaying the predicted HR.

2. The device of claim 1, wherein the first sensor is a photoplethysmogram (PPG) sensor and the time domain raw HR signals are time domain raw PPG signals.

3. The device of claim 1, wherein the combination of the FD PC1 and FD PC2 acceleration signal waveforms is of the form A{FD PC1 acceleration signal waveform}+B{FD PC2 acceleration signal waveform} respectively where A and B are scale factors.

4. The device of claim 3, wherein the scale factors A and B are determined by a successive approximation algorithm such as to minimize a residual value.

5. The device of claim 1, wherein the processing circuitry is further capable of:
    generating groups of time domain raw HR signals and time domain acceleration signals such that the FD raw HR signal waveforms and the FD acceleration signal waveforms are based on discrete Fourier transforms of the groups of raw HR signals and acceleration signals; and dynamically adjusting the size of the groups in response to at least the selected frequency and previously selected frequencies.

6. A device for predicting heart rate (HR), comprising:
a first sensor configured to generate time domain raw HR signals;
a second sensor, distinct from the first sensor, configured to generate time domain acceleration signals along first, second and third directions; and
processing circuitry configured for:
performing a principal component analysis of the time domain acceleration signals along the first, second and third directions to provide time domain principal components acceleration waveforms of the time domain acceleration signals having scores along the principal component axes PC1 and PC2;
generating a frequency domain (FD) representation of the time domain raw HR signals to provide a FD raw HR signal waveform;
generating a FD representation of the time domain principal components acceleration waveforms to provide FD acceleration signal waveforms corresponding to the principal component axes PC1 and PC2, the corresponding waveforms being FD PC1 acceleration signal waveforms and FD PC2 acceleration signal waveforms respectively; and
utilizing the FD PC1 acceleration signal waveforms, the FD PC2 acceleration signal waveforms, the FD raw HR signal waveform and a plurality of spectral heart rate templates to generate a plurality of correlation values to predict the HR;
wherein the processing circuitry further configured to utilize the FD PC1 acceleration signal waveforms, the FD PC2 acceleration signal waveforms, the FD raw HR signal waveform and a plurality of spectral heart rate templates to generate a plurality of correlation values to predict the HR by:
forming a combination of the FD PC1 and FD PC2 acceleration signal waveforms; subtracting the combination of the FD PC1 and FD PC2 acceleration signal waveforms from the FD raw HR signal waveform to obtain a FD projected HR signal waveform;
correlating the FD projected HR signal waveform with the plurality of spectral heart rate templates to generate the plurality of correlation values;
predicting a heart rate based on the highest correlation value among the plurality of correlation values; and
displaying the predicted HR.

7. The device of claim 6, wherein the first sensor is a photoplethysmogram (PPG) sensor and the time domain raw HR signals are time domain raw PPG signals.

8. The device of claim 6, wherein the combination of the FD PC1 and FD PC2 acceleration signal waveforms is of the form A{FD PC1 acceleration signal waveform}+B{FD PC2 acceleration signal waveform} respectively where A and B are scale factors.

9. The device of claim 8, wherein the scale factors A and B are determined by a successive approximation algorithm such as to minimize a residual value.

10. The device of claim 6, wherein the processing circuitry is further capable of:
generating groups of time domain raw HR signals and time domain acceleration signals such that the FD raw HR signal waveforms and the FD acceleration signal waveforms are based on discrete Fourier transforms of the groups of raw HR signals and acceleration signals; and
dynamically adjusting the size of the groups in response to at least the correlation values.

11. The device of claim 10, wherein the processing circuitry is further capable of dynamically adjusting the size of the groups dependent on a currently predicted HR, a previously predicted HR and correlation values associated with the currently predicted HR and the previously predicted HR.

12. A method for predicting heart rate (HR), comprising:
generating time domain raw HR signals from a first sensor;
generating time domain acceleration signals along first, second and third directions from a second sensor, distinct from the first sensor;
configuring processing circuitry for:
performing a principal component analysis of the time domain acceleration signals along the first, second and third directions to provide time domain principal components acceleration waveforms of the time domain acceleration signals having scores along the principal component axes PC1 and PC2;
generating a frequency domain (FD) representation of the time domain raw HR signals to provide a FD raw HR signal waveform;
generating a FD representation of the time domain principal components acceleration waveforms to provide FD acceleration signal waveforms corresponding to the principal component axes PC1 and PC2 and designating the corresponding waveforms as FD PC1 acceleration signal waveforms and FD PC2 acceleration signal waveforms respectively; and
utilizing the FD PC1 acceleration signal waveforms, the FD PC2 acceleration signal waveforms and the FD raw HR signal waveform to predict the HR;
forming a combination of the FD PC1 and FD PC2 acceleration signal waveforms;
subtracting the combination of the FD PC1 and FD PC2 acceleration signal waveforms from the FD raw HR signal waveform to obtain a FD projected HR signal waveform;
selecting a frequency corresponding to the maximum peak of the FD projected HR signal waveform;
predicting a HR based on the selected frequency; and
displaying the predicted HR.

13. The method of claim 12, wherein the time domain raw HR signals is generated from a photoplethysmogram (PPG) sensor.

14. The method of claim 12, wherein the combination of the FD PC1 and FD PC2 acceleration signal waveforms is of the form A{FD PC1 acceleration signal waveform}+B{FD PC2 acceleration signal waveform} respectively where A and B are scale factors.

15. The method of claim 14, wherein the scale factors A and B are determined by a successive approximation algorithm such as to minimize a residual value.

16. The method of claim 12, further comprising:
generating groups of time domain raw HR signals and time domain acceleration signals such that the FD raw HR signal waveforms and the FD acceleration signal waveforms are based on discrete Fourier transforms of the groups of raw HR signals and acceleration signals; and dynamically adjusting the size of the groups in response to at least the selected frequency and previously selected frequencies.

17. A method for predicting heart rate (HR), comprising:
generating time domain raw HR signals from a first sensor;
generating time domain acceleration signals along first, second and third directions from a second sensor, distinct from the first sensor;
configuring processing circuitry for:
performing a principal component analysis of the time domain acceleration signals along the first, second and third directions to provide time domain principal components acceleration waveforms of the time domain acceleration signals having scores along the principal component axes PC1 and PC2;
generating a frequency domain (FD) representation of the time domain raw HR signals to provide a FD raw HR signal waveform;
generating a FD representation of the time domain principal components acceleration waveforms to provide FD acceleration signal waveforms corresponding to the principal component axes PC1 and PC2 and designating the corresponding waveforms as FD PC1 acceleration signal waveforms and FD PC2 acceleration signal waveforms respectively; and
utilizing the FD PC1 acceleration signal waveforms, the FD PC2 acceleration signal waveforms, the FD raw HR signal waveform and a plurality of spectral heart rate templates to generate a plurality of correlation values to predict the HR;
forming a combination of the FD PC1 and FD PC2 acceleration signal waveforms;
subtracting the combination of the FD PC1 and FD PC2 acceleration signal waveforms from the FD raw HR signal waveform to obtain a FD projected HR signal waveform;
correlating the FD projected HR signal waveform with the plurality of spectral heart rate templates to generate the plurality of correlation values;
predicting a heart rate based on the highest correlation value among the plurality of correlation values; and
displaying the predicted HR.

* * * * *